United States Patent
Guan et al.

(10) Patent No.: US 9,556,113 B2
(45) Date of Patent: Jan. 31, 2017

(54) COMBINATION USES OF DICHLOROACETATE AND OXAMATE, AND THEIR PRODRUGS, FOR CANCER TREATMENT

(71) Applicants: The South Dakota Board of Regents, Pierre, SD (US); Sanford Research, Sioux Falls, SD (US)

(72) Inventors: Xiangming Guan, Brookings, SD (US); Chandrahar Dwivedi, Brookings, SD (US); Yinghong Li, Beijing (CN); Yang Yang, Brookings, SD (US); John H. Lee, Sioux Falls, SD (US); Wilson Keith Miskimins, Alcester, SD (US)

(73) Assignees: The South Dakota Board of Regents, Pierre, SD (US); Sanford Research, Sioux Falls, SD (US)

( * ) Notice: Subject to any disclaimer, the term of this patent is extended or adjusted under 35 U.S.C. 154(b) by 0 days.

(21) Appl. No.: 14/699,946

(22) Filed: Apr. 29, 2015

(65) Prior Publication Data

US 2015/0315131 A1 Nov. 5, 2015

Related U.S. Application Data

(60) Provisional application No. 61/985,876, filed on Apr. 29, 2014.

(51) Int. Cl.
| | |
|---|---|
| *C07C 235/74* | (2006.01) |
| *A61K 45/06* | (2006.01) |

(Continued)

(52) U.S. Cl.
CPC .............. *C07C 235/74* (2013.01); *A61K 9/008* (2013.01); *A61K 9/0019* (2013.01); *A61K 9/06* (2013.01);

(Continued)

(58) Field of Classification Search
None
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |

(Continued)

OTHER PUBLICATIONS

Database Caplus Chemical Abstracts Service, Columbus, Ohio, US; Database Accession No. 1935:55842, Abstract of Helgeson et al., Proceedings of the South Dakota Academy of Science (1935), 14, 22-26.*

(Continued)

*Primary Examiner* — Karl J Puttlitz
(74) *Attorney, Agent, or Firm* — Billion & Armitage; Patti J. Jurkovich

(57) ABSTRACT

The invention novel compounds, pharmaceutical compositions and methods useful for preventing or treating cancer in animals and humans. Also, the invention provides novel prodrugs useful for reducing tumor size, and inhibiting the growth of cancers, inhibiting tumor cell growth and tumor cell proliferation, and promoting apoptosis of tumor cells. When used in combination with chemoradiation therapy, the novel compounds, compositions and prodrugs provided herein can improve the effectiveness of chemoradiation therapy. The novel compounds, compositions and prodrugs of the invention inhibit PDK and LDH in unique and effective ways.

5 Claims, 20 Drawing Sheets

Dichloroacetic acid sodium salt (DCA)

Oxamic acid sodium salt (Oxamate)

(51) Int. Cl.

| | |
|---|---|
| A61N 5/10 | (2006.01) |
| A61K 31/225 | (2006.01) |
| C07C 233/56 | (2006.01) |
| A61K 33/24 | (2006.01) |
| A61K 9/00 | (2006.01) |
| A61K 47/02 | (2006.01) |
| A61K 47/10 | (2006.01) |
| A61K 47/14 | (2006.01) |
| A61K 47/18 | (2006.01) |
| A61K 47/26 | (2006.01) |
| A61K 9/06 | (2006.01) |
| A61K 47/32 | (2006.01) |
| A61K 9/08 | (2006.01) |
| A61K 47/38 | (2006.01) |
| A61K 47/44 | (2006.01) |
| A61K 9/20 | (2006.01) |
| A61K 9/48 | (2006.01) |

(52) U.S. Cl.
CPC .............. *A61K 9/08* (2013.01); *A61K 9/2018* (2013.01); *A61K 9/2027* (2013.01); *A61K 9/2054* (2013.01); *A61K 9/2059* (2013.01); *A61K 9/4858* (2013.01); *A61K 9/4866* (2013.01); *A61K 31/225* (2013.01); *A61K 33/24* (2013.01); *A61K 45/06* (2013.01); *A61K 47/02* (2013.01); *A61K 47/10* (2013.01); *A61K 47/14* (2013.01); *A61K 47/18* (2013.01); *A61K 47/26* (2013.01); *A61K 47/32* (2013.01); *A61K 47/38* (2013.01); *A61K 47/44* (2013.01); *A61N 5/10* (2013.01); *C07C 233/56* (2013.01); *A61N 2005/1098* (2013.01)

(56) References Cited

U.S. PATENT DOCUMENTS

| | | |
|---|---|---|
| 4,820,508 A | 4/1989 | Wortzman |
| 4,938,949 A | 7/1990 | Borch et al. |
| 4,992,478 A | 2/1991 | Geria |

OTHER PUBLICATIONS

Database Caplus Chemical Abstracts Service, Columbus, Ohio, US; Database Accession No. 1911:9639, Abstract of Alpern et al., Proceedings of the Chemical Society, London (1911), 26, 345.*
The Organic Chemistry of Drug Design and Drug Action, Silverman, Academic Press, 1992, pp. 352-355.*
Database Caplus Chemical Abstracts Service, Columbus, Ohio, US; Database Accession No. 1947:8984, Abstract of GB 580184 TeGrotenhuis et al., The General Tire & Rubber Co., Aug. 29, 1964.*
Database Caplus Chemical Abstracts Service, Columbus, Ohio, US; Database Accession No. 1961:32807, Abstract of Kozlova et al., Vysokomolekulyarnye Soedineniya (1960), 2, 614-18.*
Abdelmalak et al., "Long-term safety of dichloroacetate in congenital lactic acidosis", Molecular Genetics and Metabolism, vol. 109 (2), 2013, pp. 139-143.
Aykin-Burns et al., "Sensitivity to low-dose/low-LET ionizing radiation in mammalian cells harboring mutations in succinate dehydrogenase subunit C is governed by mitochondria-derived reactive oxygen species", Radiation Research, vol. 175 (2), 2011, pp. 150-158.
Ayyanathan et al., "Combination of Sulindac and Dichloroacetate Kills Cancer Cells via Oxidative Damage", PloS One, vol. 7 (7), 2012, pp. 1-12.
Bailey et al., "Targeting the metabolic microenvironment of tumors", Advances of Pharmacology, vol. 65, 2012, pp. 63-107.
Bensaad et al., "TIGAR, a p53-inducible regulator of glycolysis and apoptosis", Cell, vol. 126 (1), 2006, pp. 107-120.
Bonnet et al., "A mitochondria-K+ channel axis is suppressed in cancer and its normalization promotes apoptosis and inhibits cancer growth", Cancer Cell, vol. 11 (1), 2007, pp. 37-51.
Brahimi-Horn et al., "Expression of a truncated active form of VDAC1 in lung cancer associates with hypoxic cell survival and correlates with progression to chemotherapy resistance", Cancer Research, vol. 72 (8), 2012, pp. 2140-2150.
Broggini-Tenzer et al., "Metabolism of tumors under treatment: Mapping of metabolites with quantitative bioluminescence", Radiotherapy and Oncology, vol. 99 (3), 2011, pp. 398-403.
Buzzai et al., "The glucose dependence of Akt-transformed cells can be reversed by pharmacologic activation of fatty acid beta-oxidation", Oncogene, vol. 24 (26), 2005, pp. 4165-4173.
Choi, et al., "Generation of oxamic acid libraries: antimalarials and inhibitors of Plasmodium falciparum lactate dehydrogenase", J Comb Chem, vol. 9 (2), 2007, pp. 292-300.
Coppock et al., "Improved Clearance during Treatment of HPV-Positive Head and Neck Cancer through mTOR Inhibition", Neoplasia, vol. 15 (6), 2013, pp. 620-630.
Duan et al., "Antitumor activity of dichloroacetate on C6 glioma cell: in vitro and in vivo evaluation", Onco Targets and Therapy, vol. 6, 2013, pp. 189-198.
Dunbar et al., "Phase 1 trial of dichloroacetate (DCA) in adults with recurrent malignant brain tumors", Investigational New Drugs, vol. 32 (3), 2014, pp. 452-464.
Elstrom et al., "Akt stimulates aerobic glycolysis in cancer cells", Cancer Research, vol. 64 (11), 2004, pp. 3892-3899.
Fiebiger et al., "In vitro cytotoxicity of novel platinum-based drugs and dichloroacetate against lung carcinoid cell lines", Clinical & Translational Oncology: Official Publication of the Federation of Spanish Oncology Societies and of the National Cancer Institute of Mexico, vol. 13 (1), 2011, pp. 43-49.
Fiume et al., "Impairment of aerobic glycolysis by inhibitors of lactic dehydrogenase hinders the growth of human hepatocellular carcinoma cell lines", Pharmacology, vol. 86 (3), 2010, pp. 157-162.
Fiume et al., "Inhibition of lactic dehydrogenase as a way to increase the anti-proliferative effect of multi-targeted kinase inhibitors", Pharmacological Research: The Official Journal of the Italian Pharmacological Society, vol. 63 (4), 2011, pp. 328-334.
Garon et al., "Dichloroacetate should be considered with platinum-based chemotherapy in hypoxic tumors rather than as a single agent in advanced non-small cell lung cancer", Journal of Cancer Research and Clinical Oncology, vol. 140 (3), 2014, pp. 443-452.
Gatenby et al., "Why do cancers have high aerobic glycolysis?", Nature Reviews Cancer, vol. 4, 2004, pp. 891-899.
Goetze et al., "Lactate enhances motility of tumor cells and inhibits monocyte migration and cytokine release", International Journal of Oncology, vol. 39 (2), 2011, pp. 453-463.
Goldberg et al., "The role of glycolysis in the growth of tumor cells IV. The basis of glucose toxicity in oxamate-treated, cultured cells", The Journal of Biological Chemistry, vol. 240 (7), 1965, pp. 2791-2796.
Goldberg et al., "The role of glycolysis in the growth of tumor cells. III. Lactic dehydrogenase as the site of action of oxamate on the growth of cultured cells", The Journal of Biological Chemistry, vol. 240 (7), 1965, pp. 2786-2790.
Gottfried et al., "Tumor-derived lactic acid modulates dendritic cell activation and antigen expression", Blood, vol. 107 (5), 2006, pp. 2013-2021.
Granchi et al., "Inhibitors of lactate dehydrogenase isoforms and their therapeutic potentials", Current Medicinal Chemistry, vol. 17 (7), 2010, pp. 672-697.
Heiden et al., "Understanding the Warburg Effect: The Metabolic Requirements of Cell Proliferation", Science, vol. 324, 2009, pp. 1029-1033.
Hoover et al., "The role of human papillomavirus 16 E6 in anchorage-independent and invasive growth of mouse tonsil epithelium", Arch Otolaryngol Head Neck Surg., vol. 133 (5), 2013, pp. 495-502.
Hu et al., "K-ras(G12V) transformation leads to mitochondrial dysfunction and a metabolic switch from oxidative phosphorylation to glycolysis", Cell Research, vol. 22 (2), 2012, pp. 399-412.

(56) References Cited

OTHER PUBLICATIONS

Jang et al., "Cancer cell metabolism: implications for therapeutic targets", Experimental & Molecular Medicine, vol. 45, 2013, 8 pages.
Kailavasan et al., "NMR-based evaluation of the metabolic profile and response to dichloroacetate of human prostate cancer cells", NMR Biomedicine, vol. 27 (5), 2014, pp. 610-616.
Ke et al., "Hypoxia-Inducible Factor-1 (HIF-1)", Molecular Pharmacology, vol. 70 (5), 2006, pp. 1469-1480.
Kluza et al., "Inactivation of the HIF-1α/PDK3 signaling axis drives melanoma toward mitochondrial oxidative metabolism and potentiates the therapeutic activity of pro-oxidants", Cancer Research, vol. 72 (19), 2012, pp. 5035-5047.
Koukourakis et al., "Lactate dehydrogenase 5 expression in squamous cell head and neck cancer relates to prognosis following radical or postoperative radiotherapy", Oncology, vol. 77 (5), 2009, pp. 285-292.
Kumar et al., "Antitumor and chemosensitizing action of dichloroacetate implicates modulation of tumor microenvironment: A role of reorganized glucose metabolism, cell survival regulation and macrophage differentiation", Toxicology and Applied Pharmacology, vol. 273 (1), 2013, pp. 196-208.
Le et al., "Inhibition of lactate dehydrogenase A induces oxidative stress and inhibits tumor progression", Proceedings of the National Academy of Sciences of the United States of America, vol. 107 (5), 2010, pp. 2037-2042.
Li et al., "Effective inhibition of nasopharyngeal carcinoma in vitro and in vivo by targeting glycolysis with oxamate", International Journal of Oncology, vol. 43 (5), 2013, pp. 1710-1718.
Liu et al., "Metabolism targeting therapy of dichloroacetate-loaded electrospun mats on colorectal cancer", Drug Delivery, vol. 22 (1), 2015, pp. 136-143.
Loscalzo, "The cellular response to hypoxia: tuning the system with microRNAs", The Journal of Clinical Investigation, vol. 120, 2010, pp. 3815-3817.
Michelakis et al., "Dichloroacetate (DCA) as a potential metabolic-targeting therapy for cancer", British Journal of Cancer, vol. 99 (7), 2008, pp. 989-994.
Michelakis et al., "Metabolic Modulation of Glioblastoma with Dichloroacetate", Science Translational Medicine, vol. 2 (31), 2010, pp. 31ra34.
Morfouace et al., "Comparison of spheroids formed by rat glioma stem cells and neural stem cells reveals differences in glucose metabolism and promising therapeutic applications", The Journal of Biological Chemistry, vol. 287 (40), 2012, pp. 33664-33674.
Papaconstantinou et al., "The role of glycolysis in the growth of tumor cells. I. Effects of oxamic acid on the metabolism of Ehrlich ascites tumor cells in vitro", The Journal of Biological Chemistry, vol. 236, 1961, pp. 278-284.
Papaconstantinou et al., "The role of glycolysis in the growth of tumor cells. II. The effect of oxamic acid on the growth of HeLa cells in tissue culture", The Journal of Biological Chemistry, vol. 236, 1961, pp. 285-288.
Paris et al., "Glycerides as prodrugs. 1. Synthesis and antiinflammatory activity of 1,3-bis(alkanoyl)-2-(O-acetylsalicyloyl)glycerides (aspirin triglycerides)", Journal of Medicinal Chemistry, vol. 22 (6), 1979, pp. 683-687.
Paris et al., "Glycerides as prodrugs. 2. 1,3-Dialkanoyl 2 (2 methyl-4-oxo-1,3-benzodioxan-2-yl)glycerides (cyclic aspirin triglycerides) as antiinflammatory agents", Journal of Medicinal Chemistry, vol. 23 (1), 1980, pp. 79-82.
Paris et al., "Glycerides as prodrugs. 3. Synthesis and antiinflammatory activity of [1-(p-chlorobenzoyl)-5-methoxy-2-methylindole-3-acetyl] glycerides (indomethacin glycerides)", Journal of Medicinal Chemistry, vol. 23 (1), 1980, pp. 9-13.
Pathak et al., "Mito-DCA: A Mitochondria Targeted Molecular Scaffold for Efficacious Delivery of Metabolic Modulator Dichloroacetate", ACS Chemical Biology, vol. 9 (5), 2014, pp. 1178-1187.
Remillard et al., "Activation of K+ channels: an essential pathway in programmed cell death", American Journal of Physiology Lung Cellular and Molecular Physiology, vol. 286 (1), 2011, pp. L49-L67.
Ruckenstuhl et al., "The Warburg Effect Suppresses Oxidative Stress Induced Apoptosis in a Yeast Model for Cancer", PloS One, vol. 4 (2), 2009, pp. 1-6.
Saed et al., "Dichloroacetate induces apoptosis of epithelial ovarian cancer cells through a mechanism involving modulation of oxidative stress", Reproductive Sciences, vol. 18 (12), 2011, pp. 1253-1261.
Semenza, "Hypoxia-inducible factor 1: regulator of mitochondrial metabolism and mediator of ischemic preconditioning", Biochimica Biophysica Acta, vol. 1813 (7), 2011, pp. 1263-1268.
Semenza, "Tumor metabolism: cancer cells give and take lactate", Journal of Clinical Investigation, vol. 118 (12), 2008, pp. 3835-3837.
Shime et al., "Tumor-secreted lactic acid promotes IL-23/IL-17 proinflammatory pathway", Journal of Immunology, vol. 180 (11), 2008, pp. 7175-7183.
Sonveaux et al., "Targeting lactate-fueled respiration selectively kills hypoxic tumor cells in mice", The Journal of Clinical Investigation, vol. 118 (12), 2008, pp. 3930-3942.
Warburg, "On the Origin of Cancer Cells", Science, vol. 123 (3191), 1956, pp. 309-314.
Xuan et al., "Dichloroacetate attenuates hypoxia-induced resistance to 5-fluorouracil in gastric cancer through the regulation of glucose metabolism", Experimental Cell Research, vol. 321 (2), 2014, pp. 219-230.
Zhai et al., "Inhibition of LDH-A by oxamate induces G2/M arrest, apoptosis and increases radiosensitivity in nasopharyngeal carcinoma cells", Oncology Reports, vol. 30 (6), 2013, pp. 2983-2991.
Zhou et al., "Warburg effect in chemosensitivity: Targeting lactate dehydrogenase-A re-sensitizes Taxol-resistant cancer cells to Taxol", Molecular Cancer, vol. 9, 2010, pp. 1-12.

* cited by examiner a. Tetrahydrofuran (THF) 30 mL, room temperature, overnight

A

B 5 min

1

Oxamate

DCA 25 min

1

Oxamate

DCA 5 min

2

Oxamate

DCA 25 min

Oxamate

DCA

COMBINATION USES OF DICHLOROACETATE AND OXAMATE, AND THEIR PRODRUGS, FOR CANCER TREATMENT

CROSS-REFERENCE TO RELATED APPLICATION

This application claims benefit of Application No. 61/985,876, filed 29 Apr. 2014 in the U.S. and which application is incorporated herein by reference. A claim of priority is made.

GOVERNMENT SUPPORT

This invention was made with a support from South Dakota Office of Economic Development through a grant to The Translational Cancer Research Center.

BACKGROUND OF THE INVENTION

Cancer is the second most common cause of death in the U.S., accounting for nearly 1 of every 4 deaths. Based on Cancer Facts & Figures. 2014 from American Cancer Society, an estimated 1,665,540 new cancer cases will be diagnosed and 585,720 cancer deaths are estimated in the U.S. in 2014. Solid tumors are a serious human health concern throughout the world, as they comprise the majority of cancer incidences and mortalities.

Currently, there is a need for therapeutic agents that are useful for treating cancer.

SUMMARY OF THE INVENTION

The present invention provides pharmaceutical compositions. The pharmaceutical compositions comprise one or more compounds of formulas (I) through (XIX), and a pharmaceutically acceptable diluent or carrier. The pharmaceutical compositions can optionally comprise one or more anticancer agents. In certain embodiments, the compounds are prodrugs.

Certain embodiments of the invention are methods of preventing or treating cancer in a mammal (e.g., human). Each method comprises administering to the mammal an effective amount of one or more compounds of the present invention. Each method may optionally comprise administering to the mammal one or more anticancer agents or one or more effective doses of chemoradiation. In certain embodiments, the pharmaceutical compositions comprise one or more prodrugs. In other embodiments, the compounds of formulas (I) through (XIX) are prodrugs.

The invention provides methods of preventing or treating a tumor in a mammal (e.g., human). In embodiment, the tumor is a solid tumor. The methods comprise administering to the mammal an effective amount of one or more pharmaceutical compositions of the present invention.

The present invention also provides intermediates and methods of making (e.g., synthetically preparing) compounds of formulas (I) through (XIX). Also provided are methods of making prodrugs.

The invention provides novel compounds of formulas (I) through (XIX) or a pharmaceutically acceptable salt or prodrug thereof. In certain embodiments, the invention provides novel compounds of formula (I), (II), (V), (XI), or (XVI), or a pharmaceutically acceptable salt or prodrug thereof, intermediates for the synthesis of compounds of formula (I), (II), (V), (XI), or (XVI), as well as methods of preparing compounds of formula (I), (II), (V), (XI), or (XVI), or a pharmaceutically acceptable salt thereof. The invention also provides compounds of formula (I), (II), (V), (XI), or (XVI) that are useful as intermediates for the synthesis of other useful compounds. The invention provides for the use of compounds of formula (I), (II), (V), (XI), or (XVI), or a pharmaceutically acceptable salt thereof, for the manufacture of medicaments useful for the treatment of cancer in a mammal, such as a human.

Accordingly, in one embodiment the invention also provides a composition comprising a compound of formula (I), (II), (V), (XI), or (XVI), or a pharmaceutically acceptable salt thereof, at least one other therapeutic agent, and a pharmaceutically acceptable diluent or carrier. The invention also provides a kit comprising a compound of formula (I), (II), (V), (XI), or (XVI), or a pharmaceutically acceptable salt thereof, at least one other therapeutic agent, packaging material, and instructions for administering the compound or the pharmaceutically acceptable salt thereof and the other therapeutic agent or agents to an animal to treat cancer.

The invention provides for the use of the compositions described herein for use in medical therapy. The medical therapy can be treating cancer, for example, breast cancer, lung cancer, pancreatic cancer, prostate cancer, brain, liver, bladder, or colon cancer. The invention also provides for the use of a composition as described herein for the manufacture of a medicament to treat a disease in a mammal, for example, cancer in a human. The medicament can include a pharmaceutically acceptable diluent, excipient, or carrier.

The invention provides a composition comprising an amount of dichloroacetate and an amount of oxamate, and a pharmaceutically acceptable carrier.

The invention also provides a compound comprising

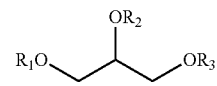

wherein $R_1$ is H, oxamate, —C(O)C(O)N($R_4$)($R_5$), dichloroacetate, —C(O)CCl$_3$, —C(O)CH$_2$Cl, or R*, $R_2$ is H, oxamate, —C(O)C(O)N($R_4$)($R_5$), dichloroacetate, —C(O)CCl$_3$, —C(O)CH$_2$Cl, or R*, and $R_3$ is H, oxamate, —C(O)C(O)N($R_4$)($R_5$), dichloroacetate, —C(O)CCl$_3$, —C(O)CH$_2$Cl, or R*, wherein R* is a diacid or an amino acid, or an alkyl group such as methyl, ethyl, ($C_1$-$C_{20}$)alkyl group or ($C_3$-$C_{16}$)cycloalkyl group, or an aryl group such as a phenyl, a naphthanyl group, or a ($C_6$-$C_{14}$)aryl group, or heterocyclics, such as furan, pyridine, imidazole, or a pharmaceutically acceptable salt or prodrug thereof. $R_4$ and $R_5$ can be an alkyl group, such as methyl, ethyl, ($C_1$-$C_{20}$)alkyl group or ($C_3$-$C_{16}$)cycloalkyl group, or an aryl group such as a phenyl, a naphthanyl group, or a ($C_6$-$C_{14}$)aryl group, or heterocyclics, such as furan, pyridine, imidazole, or a pharmaceutically acceptable salt or prodrug thereof. In certain embodiments of the compounds of the invention, $R_1$ and $R_3$ are each dichloroacetate, —C(O)CCl$_3$, or —C(O)CH$_2$Cl. In other embodiments of the compounds of the invention, $R_1$ and $R_2$ are each dichloroacetate, or, —C(O)CCl$_3$, or —C(O)CH$_2$Cl. In still other embodiments of the compounds of the invention, $R_1$ is dichloroacetate, —C(O)CCl$_3$, or —C(O)CH$_2$Cl, and $R_2$ or $R_3$ is oxamate or —C(O)C(O)N($R_4$)($R_5$). The invention also provides a pharmaceutical composition comprising one or more compounds of the invention, or a pharmaceutically acceptable salt or prodrug thereof, and a pharmaceutically acceptable carrier.

Also provided are methods of treating cancer in an animal, comprising administering to the animal an effective amount of one or more of the compositions of the invention. Further provided are methods for treating cancer in an animal, comprising administering to the animal an effective amount of a compound of the invention, or a combination thereof.

In certain embodiments, provided are methods of inhibiting the growth of tumor cells in an animal, comprising administering to the animal an effective amount of a compound of the invention, or a combination thereof. In some embodiments of the methods of the invention, one or more of the compounds are prodrugs. Optionally, the methods of the invention may further comprise administering an effective amount of at least one other therapeutic agent to said animal.

Also provided are methods of inhibiting the growth of tumor cells in an animal, comprising contacting said tumor cells with an effective amount of one or more of the compositions of the invention. In addition, provided are methods of inhibiting tumor cell proliferation in an animal, comprising administering to said animal an effective amount of one or more compounds of the invention, or a combination thereof. Certain methods of the invention optionally provide for administering to the animal one or more effective doses of chemoradiation. A further embodiment includes a pharmaceutical composition comprising one or more compounds as described herein above, or the pharmaceutically acceptable salts or prodrugs thereof, and a pharmaceutically acceptable carrier. In a further embodiment, provided are methods of synthesizing the compounds and prodrugs as described or provided herein.

Additionally, another embodiment provides a pharmaceutical composition comprising an amount of at least one prodrug as described herein, and an amount of DCA, or a pharmaceutically acceptable salt or prodrug thereof, and a pharmaceutically acceptable carrier.

Embodiments also include methods for treating cancer in an animal, comprising administering to an animal afflicted therewith an effective amount of one or more compositions provided or described herein. The methods described herein optionally include the administration of at least one prodrug of the compounds described herein. Further, the methods described herein also comprise the option of administering to the animal an effective amount of at least one other therapeutic agent, an effective amount of one or more anticancer agents, one or more effective doses of chemoradiation, or a combination thereof. The treatments provided by the methods provided herein are effective to provide a beneficial effect to the animal. In certain embodiments, the animal is a mammal. In other embodiments, the animal is a human.

Another embodiment provides a method of inhibiting the growth of tumor cells in an animal, comprising administering to an animal an effective amount of one or more compositions provided or described herein. Optionally, the methods may include the administration of at least one prodrug of the compositions or compounds provided herein. In some embodiments, the methods optionally include administering to the animal an effective amount of at least one other therapeutic agent, an effective amount of one or more anticancer agents, one or more effective doses of chemoradiation, or a combination thereof.

Another embodiment provides a method of inhibiting the tumor growth in an animal, comprising administering to an animal an effective amount of one or more compositions provided or described herein. Optionally, the methods may include the administration of at least one prodrug of the compositions or compounds provided herein. In some embodiments, the methods optionally include administering to the animal an effective amount of at least one other therapeutic agent, an effective amount of one or more anticancer agents, one or more effective doses of chemoradiation, or a combination thereof.

Additionally, some embodiments include methods of inhibiting tumor cell proliferation in an animal, comprising administering to the animal an effective amount of one or more compositions as provided or described herein. In still other embodiments, provided are methods of improving the effectiveness of chemotherapy by administering to an animal undergoing chemotherapy an effective amount of one or more compositions as provided or described herein.

Optionally, the methods may include administering to said animal one or more effective doses of chemoradiation. In certain embodiments of the methods, the chemoradiation is a combination of an effective amount of cisplatin and an effective amount of radiation therapy. Optionally, the method, as described herein, comprises the administration to the animal of at least one of the prodrugs of compositions as described. Further, the methods of the invention enhance apoptotic cell death in the tumors in the animal.

In further embodiments, provided are methods for sensitizing tumors to chemoradiation by administering to an animal having tumors an effective dose of one or more of the compositions described herein, followed by administering one or more effective doses of chemoradiation to the animal. In certain embodiments, the treatment provides for the reduction in the size of the tumor as compared to the size of a tumor in an animal receiving only chemoradiation therapy for the same condition.

In certain embodiments, the cancer is HPV or HNSCC or any other type of cancer.

The treatments and methods of treatment provided herein are effective to provide a beneficial effect to the animal. In certain embodiments, the animal is a mammal. In other embodiments, the animal is a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
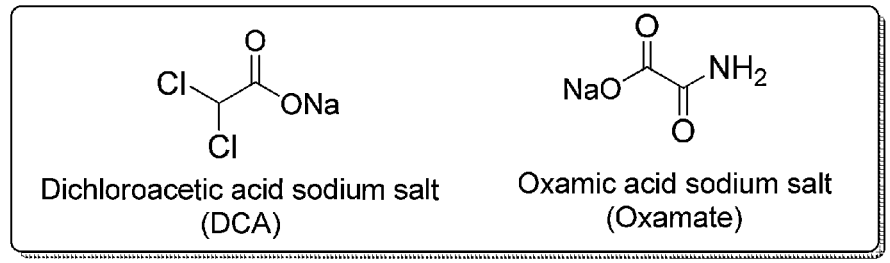
FIG. 1 illustrates the chemical structures of DCA and Oxamate.
Figure 2:
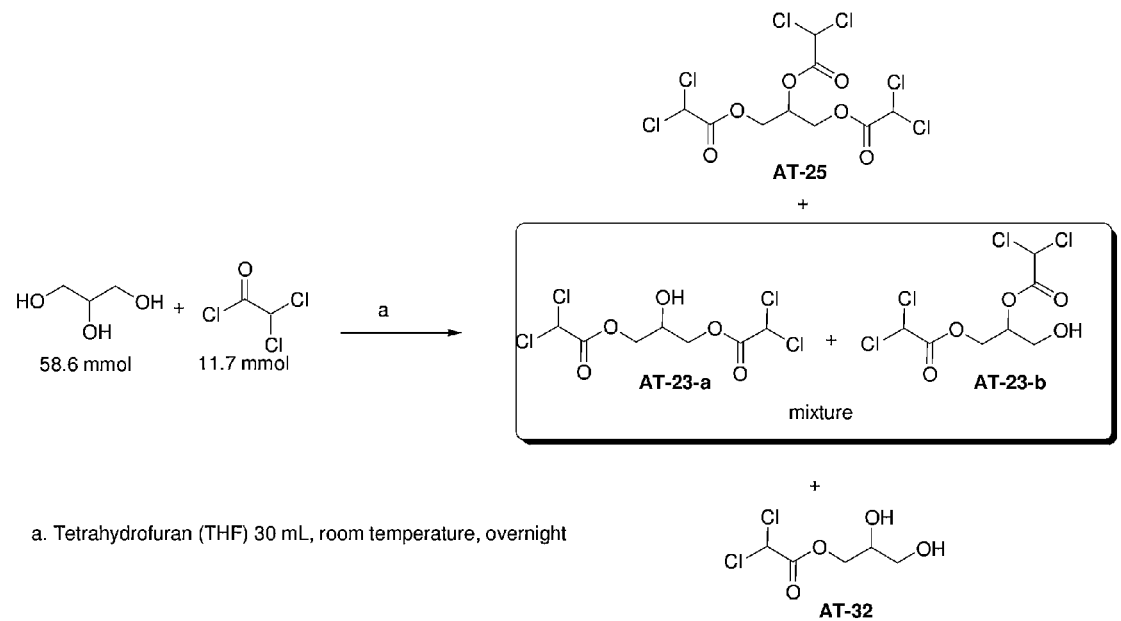
FIG. 2 illustrates the synthesis of prodrugs of DCA (AT-25, AT-32 and the mixture of AT-23-a and AT-23-b (Scheme 1). As indicated "a" denotes Tetrahydrofuran (THF) 30 ml, room temperature, overnight.
Figure 3:
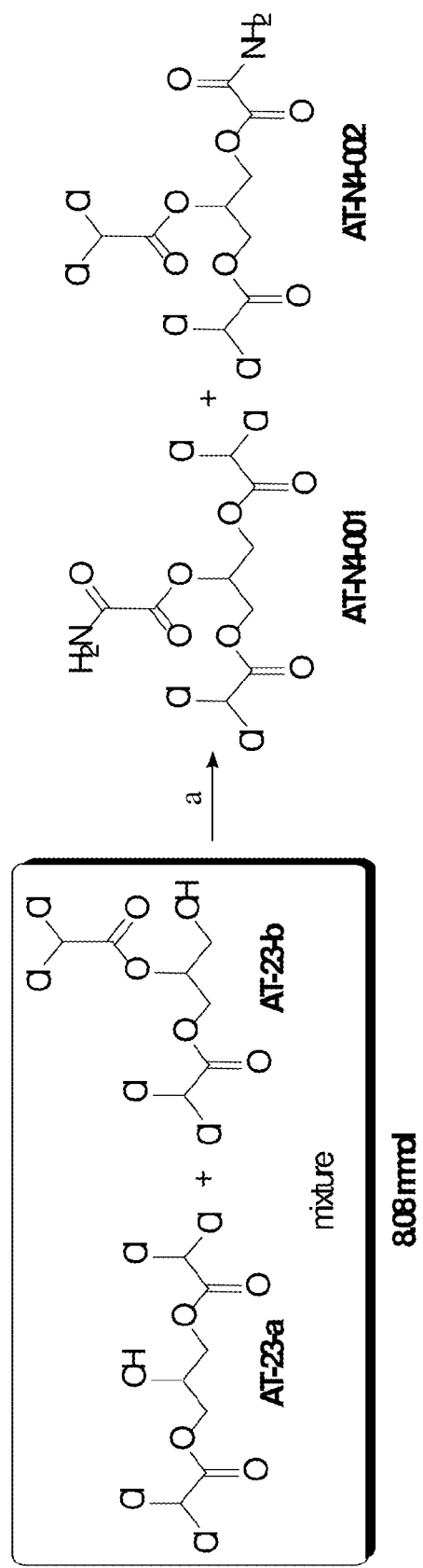
FIG. 3 illustrates the synthesis of AT-N4-001 and AT-N4-002 (Scheme 2). As indicated "a" denotes oxamic acid (8.08 mmol), 1-hydrobenzotriazole monohydrate (HOBt-H2O, 8.08 mmol), triethylamine (8.08 mmol) 1-(3-dimethylaminopropyl)-3-ethylcarbodiimide hydrochloride (8.08 mmol) in DMF (100 mL), room temperature, overnight.

Cancer cells are characterized by aerobic glycolysis even in the presence of sufficient oxygen, a phenomenon known as the Warburg effect. Most solid tumors are characterized by aerobic glycolysis, in which pyruvate is converted to lactate by the enzyme lactate dehydrogenase in cytosol (26). The Warburg effect leads to high uptake of glucose, accumulation of lactate, acidic cancer microenvironment, mitochondria dysfunction and inability to initiate apoptosis. Together, these Warburg-associated effects promote cancer growth and metastasis.

The Warburg effect has been shown to be associated with most solid tumors. The effect is characterized by a shift of glucose metabolism from normal mitochondrial oxidative metabolism to glycolysis even in the presence of enough oxygen. The unique features (high glucose uptake, high rate of glycolysis and production of lactate, acidic environment, dysfunction of mitochondria and inability of mitochondria to initiate apoptosis) associated with the Warburg effect distinct tumors from most normal tissues and provide opportunities for drug intervention to selectively inhibit tumor growth. Various approaches by targeting different aspects of the Warburg effect have been reported (5). Inhibition of PDK by DCA or inhibition of LDH by oxamate are among those approaches proven to be effective in inhibiting cancer growth through affecting two key steps of aerobic glycolysis.

Dichloroacetate (DCA) inhibits cancer growth through an increase in the influx of pyruvate into mitochondria resulting in pyruvate mitochondria oxidation and restoration of mitochondria function, and consequently apoptosis (26). This effect of DCA was achieved through inhibition of pyruvate dehydrogenase kinase (PDK). Thus, Dichloroacetate (DCA) has been demonstrated to effectively switch cancer cells from aerobic glycolysis to mitochondrial oxidative phosphorylation and restore mitochondria function through inhibition of pyruvate dehydrogenase kinase (PDK). Through inhibition of pyruvate dehydrogenase kinase, DCA makes more pyruvate dehydrogenase available for mitochondria pyruvate oxidation. DCA alone has been found effective in producing anticancer activity (26). Accordingly, DCA has undergone clinical trials for the treatment of various cancers.

Oxamate is an effective inhibitor of lactate dehydrogenase (LDH). LDH is a key enzyme involved in aerobic glycolysis. Oxamate is also a cancer growth inhibitor (33, 34). Inhibition of LDH prevents conversion of pyruvate to lactate and has been demonstrated effective in inhibiting tumor growth. Oxamate alone will cause accumulation of pyruvate but will not push pyruvate into mitochondria (26).

Applicants investigated a simultaneous inhibition of PDK and LDH, through the use of DCA and oxamate, for the effect of improving tumor's response to chemotherapy. The rationale for the combination is that inhibition of LDH by oxamate will lead to a reduction of lactate and accumulation of pyruvate. The accumulated pyruvate, that has been shown to reverse LDH inhibition by oxamate, is effectively pushed to mitochondria for oxidative metabolism by DCA through an increased PDK activity. Through the use of a head and neck cancer mouse model, Applicants demonstrated that the combined inhibition significantly improve the response of the tumor to cisplatin/radiation therapy (CRT) than either of the compounds used alone.

Applicants examined the effect on cancer growth inhibition by a combined use of DCA and oxamate with an attempt to more effectively switch aerobic glycolysis to oxidative metabolism through simultaneously inhibition of these two key steps. Applicants' data show that the dual inhibition of PDK and LDH is more effective than inhibition of each step alone confirming that the dual inhibition is an effective approach for inhibition of HPV positive HNSCCs. Applicants' data shows that their prodrugs quickly released DCA and oxamate in vivo and produced more potent effects than DCA plus oxamate.

Applicants designed prodrugs that use glycerol to connect DCA and oxamate via ester bonds. Applicants' data demonstrate that the prodrugs quickly release DCA and oxamate in mice and improve the tumor response to CRT equal to or more effective than the combination of DCA and oxamate. Applicants' findings confirm that the combined inhibition of PDK and LDH is a novel and effective approach in improving cancer chemotherapy. The data also indicate the use of the combination in treating other cancers.

It is recognized that the dosages of DCA employed in Applicants' work are in mM range, much higher compared with those considered to be potent anticancer agents. It is noted that the same concentration range of DCA has been commonly used in other pre-clinical studies (6,23,52,53). More importantly, the corresponding DCA concentration that inhibits PDK has been used to treat lactic acidosis in the clinic, as well as in clinical trials for cancer treatments (23,24,32). Therefore, the DCA concentration employed in Applicants' work is clinically relevant.

Applicants have discovered that the combined use of oxamate and DCA more effectively inhibits cancer growth than either of them given alone. The effectiveness of the combination is achieved through blocking lactate formation (oxamate) and pushing pyruvate to mitochondria for oxidative oxidation (DCA). Some features of this invention include: i) the combined inhibition of lactate dehydrogenase (oxamate) and pyruvate dehydrogenase kinase (DCA); and ii). prodrugs of the combination of oxamate+DCA using a non-toxic polyalcohol, specifically glycerol; iii). prodrugs of DCA; and iv). synthetic methods for the preparation of these prodrugs.

Applicants discovered that the combined use of DCA and oxamate reduces the formation of lactate and pushes pyruvate into mitochondria more effectively than either of them given alone, that is consistent with Applicants' rationale in proposing this simultaneous inhibition of PDK and LAH. The combined use of DCA and oxamate provides beneficial, enhanced anticancer effects in vivo and in vitro.

Applicants also provide a novel method of preparing prodrugs of DCA, using an endogenous non-toxic compound, glycerol.

Also provided is the use of an endogenous non-toxic compound, glycerol, as a linker to link DCA and oxamate together to form prodrugs of the combination of DCA and Oxamate.

The prodrugs provided herein provide many benefits, including but not limited to improved pharmaceutical and pharmacokinetic properties, and also improved targeting into cancer sites.

In some embodiments, the composition comprises a therapeutically effective amount of dichloroacetic acid sodium salt (DCA) and a therapeutically effective amount of oxamic acid sodium salt (oxamate).

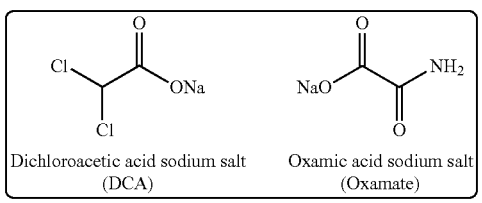

Dichloroacetic acid sodium salt (DCA)  Oxamic acid sodium salt (Oxamate)

Applicants have discovered the efficacy of prodrugs of the combination of DCA and oxamate.

Applicants' have discovered that a dual inhibition of PDK and LDH is an effective approach for improving the HPV positive HNSCCs' response to CRT. Further investigation of the dual inhibition in treating various other cancers, alone or in combination with another cancer treatment, may be warranted. The prodrugs developed and disclosed in embodiments provided herein are obtained conveniently through a two-step synthesis from two commercially available and low cost agents.

Prodrugs of DCA and Oxamate and their Analogs

The invention provides compounds of Formula I:

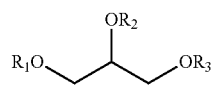

(I)

wherein $R_1$ and $R_3$ are each independently DCA, or —C(O)CCl$_3$ or —C(O)CH$_2$Cl, or a similar compound, and $R_2$ is oxamate, or —C(O)C(O)N($R_4$)($R_5$). Formula I is also referred to as AT-N4-001.

The invention further provides compounds of Formula II:

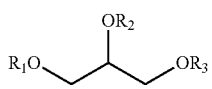

(II)

wherein $R_1$ and $R_2$ are each independently DCA, or —C(O)CCl$_3$ or —C(O)CH$_2$Cl, or similar compounds, and $R_3$ is oxamate, or —C(O)C(O)N($R_4$)($R_5$), or a similar compound. Formula II is also referred to as AT-N4-002.

The invention also provides compounds of Formula III:

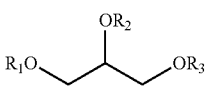

(III)

wherein $R_1$ and $R_3$ are each independently oxamate, or —C(O)C(O)N($R_4$)($R_5$) or similar compounds, and $R_2$ is DCA, or —C(O)CCl$_3$ or —C(O)CH$_2$Cl, or a similar compound.

Further provided by the invention are compounds of Formula IV:

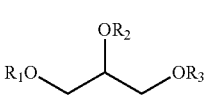

(IV)

wherein $R_1$ and $R_2$ are each independently oxamate, or —C(O)C(O)N($R_4$)($R_5$) or similar compounds, and $R_3$ is DCA, or —C(O)CCl$_3$ or —C(O)CH$_2$Cl, or a similar compound.

The invention provides compounds of Formula V:

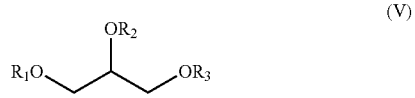

(V)

wherein $R_1$ is DCA, or —C(O)CCl$_3$ or —C(O)CH$_2$Cl, or a similar compound, and $R_2$ is H or R*, and $R_3$ is oxamate, or —C(O)C(O)N($R_4$)($R_5$), or a similar compound. Formula V is also referred to as AT-NT-003.

The invention additionally provides compounds of Formula VI:

(VI)

wherein $R_1$ is DCA, or —C(O)CCl$_3$ or —C(O)CH$_2$Cl, or a similar compound, and $R_2$ is oxamate, or —C(O)C(O)N($R_4$)($R_5$), or a similar compound, and $R_3$ is H or R*.

The invention further provides compounds of Formula VII:

(VII)

wherein $R_1$ is oxamate, or —C(O)C(O)N($R_4$)($R_5$), or a similar compound, and $R_2$ is DCA, or —C(O)CCl$_3$ or —C(O)CH$_2$Cl, or a similar compound, and $R_3$ is H or R*.

The invention provides compounds of Formula VIII:

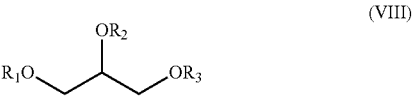

(VIII)

wherein $R_1$ is DCA, or —C(O)CCl$_3$ or —C(O)CH$_2$Cl, or a similar compound, and $R_2$ is H or R*, and $R_3$ is oxamate, or —C(O)C(O)N($R_4$)($R_5$), or a similar compound.

As used throughout this application, R* denotes any suitable functional groups that can be used in this compound to modulate physicochemical property or properties for formulation purposes and to be connected to a targeting moiety to deliver the molecule to tumor sites or locations. In certain embodiments, R* can be H.

One non-limiting example of a functional group used to modulate one or more physicochemical properties for formulation purposes is a group such as a diacid, where one acid (HOOC—COOH) forms an ester with the alcohol and the other acid makes the compound an acidic molecule. Diacids for use as functional groups include but are not limited to oxalic, malonic, succinic, glutaric, adipic, pimelic, suberic, azelaic, sebacic, undecanedioic, dodecanedioic, phthalic, isophthalic, terephthalic, carboxylic, tricarboxylic, and dicarboxylic acids as well as branched-chain diacids, alkylitaconates, fatty acid carbonates, phenyl and benzoic aklanoic acids, fatty acyl-CoA esters, and divinyl ether fatty acids. Another non-limiting example of a functional group used to modulate one or more physicochemical properties for formulation purposes is an amino acid (NH$_2$—COOH), where the acidic functional group forms an ester with the alcohol, and the amino group makes the molecule a basic molecule. Amino acids for use as functional groups include but are not limited to those grouped as aliphatic, hydroxyl or sulfur/selenium-containing, cyclic, aromatic, basic, acidic and their amides, such as glycine, alanine, valine, leucine, isoleucine, serine, systeine, selenocysteine, threonine, methionine, proline, phenylalanine, tyrosine, tryptophan, histidine, lysine, arginine, aspartate, glutamate, asparagine, glutamine. Further, the term "amino acid," comprises the residues of the natural amino acids (e.g. Ala, Arg, Asn, Asp, Cys, Glu, Gln, Gly, His, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, .alpha.-methylalanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a (C.sub.1-C.sub.6)alkyl, phenyl or benzyl ester or amide; or as an .alpha.-methylbenzyl amide).

Other suitable amino and carboxy protecting groups are known to those skilled in the art (See for example, Greene, T. W.; Wutz, P. G. M. *Protecting Groups In Organic Synthesis* second edition, 1991, New York, John Wiley & sons, Inc., and references cited therein Philip J. Kocienski; *Protecting Groups* (Georg Thieme Verlag Stuttgart, N.Y., 1994); D. Voet, *Biochemistry*, Wiley: New York, 1990; L. Stryer, *Biochemistry*, (3rd Ed.), W.H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein).

Further amino acids for use as functional groups include but are not limited glycine; aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid; amino acid amides such as glutamine and asparagine; polyamino- or polybasic-monocarboxylic acids such as arginine, lysine, β-aminoalanine, γ-aminobutyrine, ornithine, citrulline, homoarginine, homocitrulline, hydroxylysine, allohydroxylsine and diaminobutyric acid; other basic amino acid residues such as histidine; diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid; imino acids such as proline, hydroxyproline, allohydroxyproline, γ-methylproline, pipecolic acid, 5-hydroxypipecolic acid, and azetidine-2-carboxylic acid; a mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid; β-phenylserinyl; aliphatic α-amino-β-hydroxy acids such as serine, β-hydroxyleucine, β-hydroxynorleucine, β-hydroxynorvaline, and α-amino-β-hydroxystearic acid; α-amino, α-, γ-, δ- or ε-hydroxy acids such as homoserine, δ-hydroxynorvaline, γ-hydroxynorvaline and ε-hydroxynorleucine residues; canavine and canaline; γ-hydroxyornithine; 2-hexosaminic acids such as D-glucosaminic acid or D-galactosaminic acid; α-amino-β-thiols such as penicillamine, β-thiolnorvaline or β-thiolbutyrine; other sulfur containing amino acid residues including cysteine; homocysteine, β-phenylmethionine, methionine, S-allyl-L-cysteine sulfoxide, 2-thiolhistidine, cystathionine, and thiol ethers of cysteine or homocysteine; phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthylalanines; and tryptophan analogues and derivatives including kynurenine, 3-hydroxykynurenine, 2-hydroxytryptophan and 4-carboxytryptophan; α-amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-hydroxy and substituted α-hydroxy amino acids including serine, threonine, allothreonine, phosphoserine and phosphothreonine.

$R^x$ can be substituted by a second amino acid to form a dipeptide, or $R^x$ can be substituted by two amino acids to form a tripeptide, etc. Examples of two amino acid units in the compounds include the dipeptidyl groups (designated by their single letter code) AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV. Combinations of R* and these groups can be used to form a variety of compounds of Formulas provided herein.

Other non-limiting examples of functional groups used to modulate one or more physicochemical properties for formulation purposes are aliphatic substitutes, aromatic substitutes, and heterocyclics.

The term "heterocyclic" or "heterocycle" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein from 1-2 of the ring atoms is independently selected from N, NH, N($C_1$-$C_6$ alkyl), NC(O) ($C_1$-$C_6$ alkyl), O, and S; and wherein said heterocyclic ring is optionally substituted with from 1-3 independently selected $R^{a'''}$" would include (but not be limited to) tetrahydrofuryl, tetrahydropyranyl, piperidyl (piperidino), piperazinyl, morpholinyl (morpholino), pyrrolinyl, and pyrrolidinyl.

The term "heterocycloalkenyl" refers to partially unsaturated monocyclic, bicyclic, tricyclic, or other polycyclic hydrocarbon groups having one or more (e.g., 1-4) heteroatom ring atoms independently selected from O, N (it is understood that one or two additional groups may be present to complete the nitrogen valence and/or form a salt), or S. A ring carbon (e.g., saturated or unsaturated) or heteroatom can be the point of attachment of the heterocycloalkenyl substituent. Any atom can be optionally substituted, e.g., by one or more substituents. Heterocycloalkenyl groups can include, e.g., dihydropyridyl, tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclohexenyl, cyclohexadienyl, or norbornenyl.

The term "cycloalkylene" refers to a divalent monocyclic cycloalkyl group having the indicated number of ring atoms.

The term "heterocycloalkylene" refers to a divalent monocyclic heterocyclyl group having the indicated number of ring atoms.

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents.

Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group. In one aspect, the substituent(s) on a group are independently any one single, or any combination of two or more of the permissible atoms or groups of atoms delineated for that substituent. In another aspect, a substituent may itself be substituted with any one of the above substituents or groups defined above.

Further, as used herein, the phrase "optionally substituted" means unsubstituted (e.g., substituted with a hydrogen) or substituted. In certain embodiments, the term "substituted" means that a hydrogen atom is removed and replaced by a substituent. It is understood that substitution at a given atom is limited by valency.

As provided herein, $R_4$ and $R_5$ can be groups, including but not limited to, aliphatic substitutes, such as alkyl groups including but not limited to methyl, ethyl, or a ($C_1$-$C_{20}$)alkyl group or a ($C_3$-$C_{16}$)cycloalkyl group, or an aryl group such as a phenyl, a naphthanyl group, or a ($C_6$-$C_{14}$)aryl group, or heterocyclics, such as methyl, ethyl, propyl, butyl, pentyl, hexyl, octyl, or a ($C_1$ through $C_{20}$) heterocyclic group, as well as aromatic substitutes, such as phenyl, naphthanyl, phenanthrene, anthracene, chrysene, pyrene, furane, pyridine, pyrole, thiofuran, pyrimidine, thiazine, quinolone, isoquinoline, imidazole, or a pharmaceutically acceptable salt or prodrug thereof.

The invention also provides compounds of Formula IX:

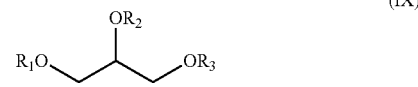

(IX)

wherein $R_1$ is DCA, or —C(O)CCl$_3$ or —C(O)CH$_2$Cl, or a similar compound, and $R_2$ is oxamate, or —C(O)C(O)N(R$_4$)(R$_5$), or a similar compound, and $R_3$ is R* or H.

Additionally, the invention provides compounds of Formula X:

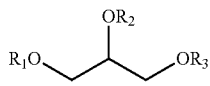

(X)

wherein $R_1$ is oxamate, or —C(O)C(O)N(R$_4$)(R$_5$), or a similar compound, and $R_2$ is DCA, or —C(O)CCl$_3$ or —C(O)CH$_2$Cl, or a similar compound, and $R_3$ is R* or H.

Prodrugs of DCA

The invention provides compounds of Formula XI:

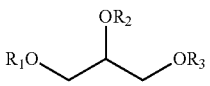

(XI)

wherein $R_1$, $R_2$ and $R_3$ are each independently DCA, or —C(O)CCl$_3$ or —C(O)CH$_2$Cl, or a similar compound. Formula XI is also referred to as AT-25.

The invention also provides compounds of Formula XII:

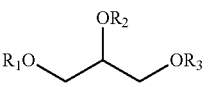

(XII)

wherein $R_1$ and $R_2$ are each independently DCA, or —C(O)CCl$_3$ or —C(O)CH$_2$Cl, or a similar compound and $R_3$ is H or R*.

The invention further provides compounds of Formula XIII:

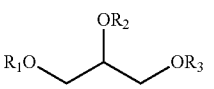

(XIII)

wherein $R_1$ and $R_3$ are each independently DCA, or —C(O)CCl$_3$ or —C(O)CH$_2$Cl, or a similar compound and $R_2$ is H or R*.

Furthermore, the invention further provides compounds of Formula XIV:

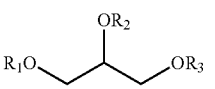

(XIV)

wherein $R_1$ and $R_2$ are each independently DCA, or —C(O)CCl$_3$ or —C(O)CH$_2$Cl, or a similar compound and $R_3$ is R* or H.

The invention provides compounds of Formula XV:

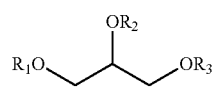

(XV)

wherein $R_1$ and $R_3$ are each independently DCA, or —C(O)CCl$_3$ or —C(O)CH$_2$Cl, or a similar compound and $R_2$ is R* or H.

Also provided by the invention are compounds of Formula XVI:

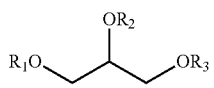

(XVI)

wherein $R_1$ is DCA, or —C(O)CCl$_3$ or —C(O)CH$_2$Cl, or a similar compound and $R_2$ and $R_3$ are each independently H or R*. Formula XVI is also referred to as AT-32.

The invention further provides compounds of Formula XVII:

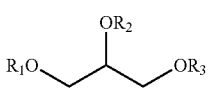

(XVII)

wherein $R_1$ and $R_3$ are each independently H or R*, and $R_2$ is DCA, or —C(O)CCl$_3$ or —C(O)CH$_2$Cl, or a similar compound.

The invention provides compounds of Formula XVIII:

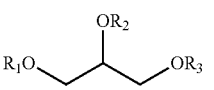

(XVIII)

wherein $R_1$ is DCA, or —C(O)CCl$_3$ or —C(O)CH$_2$Cl, or a similar compound, $R_2$ is H or R*, and $R_3$ is H or R*.

The invention further provides compounds of Formula XIX:

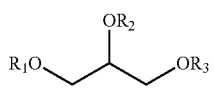

(XIX)

wherein $R_1$ is R* or H, $R_2$ is DCA, or —C(O)CCl$_3$ or —C(O)CH$_2$Cl, or a similar compound, and $R_3$ is H or R*.

The present invention provides intermediates as well as methods of making (e.g., synthetically preparing) compounds of the present invention (e.g., compounds of formulas (I) through (XIX)). The compounds of the present invention can be prepared from procedures that are known to those of skill in the art or as shown herein below. Specifically, the compounds of the present invention (e.g., compounds of formulas (I) through (XIX)) can be prepared from convenient starting materials, employing procedures (e.g., reagents and reaction conditions) known to those of skill in the art. For example, suitable reagents and reaction conditions are disclosed, e.g., in *Advanced Organic Chemistry, Part B: Reactions and Synthesis*, Second Edition, Carey and Sundberg (1983); *Advanced Organic Chemistry, Reactions, Mechanisms, and Structure*, Second Edition, March (1977); Greene, T. W., *Protecting Groups In Organic Synthesis*, Third Edition, 1999, New York, John Wiley & sons, Inc.; and *Comprehensive Organic Transformations*, Second Edition, Larock (1999). Additionally, specific exemplary procedures are shown in the examples herein below.

Discussion

Figure 12:
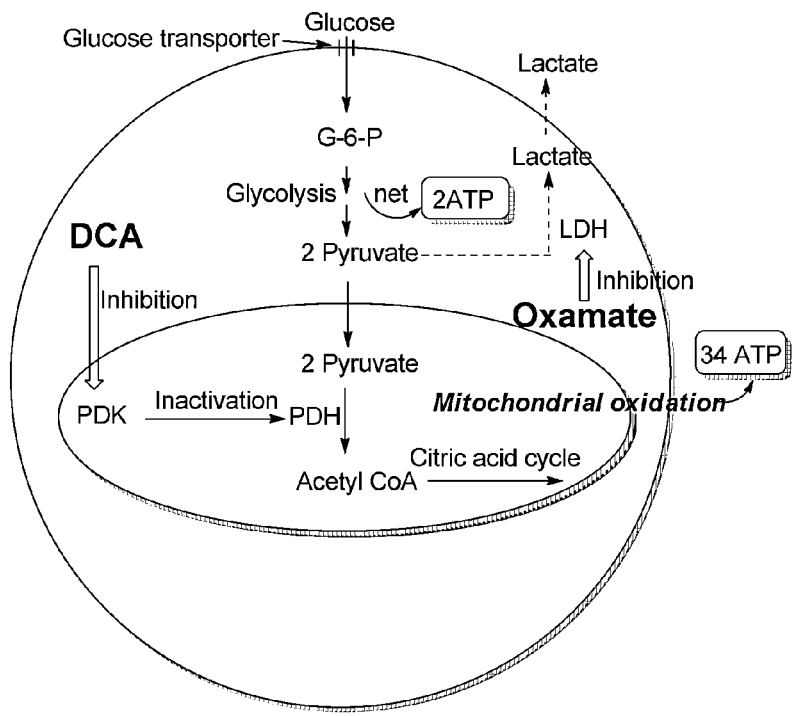
FIG. 12 illustrates glucose metabolism and inhibition of PDK and LDH for cancer growth inhibition.

Most cancers are characterized by using glycolysis as a primary energy source and source to produce biosynthetic precursors important for macromolecule biosynthesis and cell growth (1,2). In normal cells, one molecule of glucose goes through glycolysis in cytosol to produce two molecules of pyruvate with a net production of 2 ATP molecules. The process is termed as glycolysis and does not involve molecular oxygen (FIG. 12). In the presence of $O_2$ (aerobic condition), these two pyruvate molecules are transported into mitochondria where they are oxidized by $O_2$ to $CO_2$ and $H_2O$ with a release of 34 ATP molecules, a process termed as mitochondrial oxidative phosphorylation (oxidative metabolism). Therefore, a net production of 36 ATP molecules is obtained from the metabolism of one molecule of glucose under an aerobic condition. In the absence of $O_2$ (anaerobic condition), the pyruvate produced from glycolysis is converted to lactate that is transported out of the cell instead of going through oxidative metabolism (FIG. 12). In other words, under an anaerobic condition only 2 ATP molecules are obtained from one molecule of glucose with an increase in acidity due to the release of lactic acid from the cell.

Contrary to normal cells, most cancer cells employ glycolysis, even in the presence of sufficient oxygen, as the primary energy source (1-3), a phenomena known as the Warburg effect described by Otto Warburg in 1924 (4,5). The finding of the effect won Warburg the Nobel Prize in Physiology or Medicine in 1931. The inefficient use of glucose for ATP by the glycolytic process leads to a high uptake of glucose by tumor cells (1,5,6). Another phenomenon associated with the Warburg effect is accumulation of lactate that causes an increase in acidity in the tumor microenvironment. An increase in lactate inhibits host immune-mediated tumor clearance (7-9) and the increased acidity promotes cancer metastasis (5). The Warburg effect also causes dysfunction of mitochondria and inability of mitochondria to initiate apoptosis (10-12). Together, these factors promote cancer cell proliferation.

The Warburg effect is promoted by mutations in oncogenes and tumor suppressor genes (13-16) and is an adaption of cancer cellS to hypoxic environments resulted from a shortage of blood supply in cancer (3). The adaption involves an increased expression of hypoxia-inducible factor-1α (HIF-1α) aN ubiquitously expressed oxygen-sensitive transcription factor that triggers multiple responses to hypoxic conditions (3,17). HIF-1α increases the expression of lactate dehydrogenase (LDH), glucose transporters, and pyruvate dehydrogenase kinase (PDK) (18,19) (FIG. 12). LDH is responsible for the conversion of pyruvate to lactate. Glucose transporters increase uptake of glucose to meet the need of inefficient glucose metabolism by glycolysis. PDK is an enzyme that inhibits pyruvate dehydrogenase (PDH) through phosphorylation. PDH is the key enzyme in oxidative metabolism (FIG. 12). Inhibition of PDH inhibits oxidative metabolism. Together, factors resulted from the increased expression of HIF-1α shift glucose metabolism from oxidative metabolism in mitochondria to aerobic glycolysis in cytoplasm (2). This metabolic adaptation leads to dysfunction of mitochondria and suppression of apoptosis, providing a proliferative advantage in cancer cells (10-12). Switching of glucose metabolism in cancer cells from aerobic glycolysis back to oxidative metabolism can restore mitochondria function and promote apoptosis (20,21), therefore correcting the uncontrolled growth of cancer. This switch can be achieved by activating PDH as demonstrate by the use of dichloroacetate (DCA) (22,23).

DCA has been used in the clinic for the treatment of lactic acidosis since 1978. (24) Clinically, DCA has been considered safe and well tolerated with relatively modest toxicities, mostly limited to neurotoxicity (24). DCA is an inhibitor of PDK. Inhibition of PDK increases the activity of PDH and lead to more influx of pyruvate to mitochondria for oxidative metabolism over lactate production. Consequently, the inhibition results in a reduction of lactate, restoration of mitochondria function, and mitochondria ability to initiate apoptosis (25-28). The finding of DCA's effect on switching glucose metabolism in cancer cells from aerobic glycolysis to oxidative metabolism and restoring mitochondrial normal function has promoted extensive research on its use, either alone or in combination with another treatment, for the treatment of various cancers (6,22,23,25,27-31). Various clinical trials have been launched to investigate DCA alone or in combination for treating cancers like metastatic breast, non-small cell lung cancer (NSCL), brain cancer, and head and neck cancers (http://www.clinicaltrials.gov/) (23,26,32).

Another way to interfere with cancer aerobic glycolysis is through the inhibition of LDH. Inhibition of LDH blocks the conversion of pyruvate to lactate, causes pyruvate accumulation, and decreases glucose utilization without affecting oxidative metabolism (33,34). The inhibition has been explored as an effective way to inhibit cancer growth (18, 33-41) as demonstrated by the use of oxamate—an LDH inhibitor (33,34,39-41). Oxamate has been shown to inhibit cervical, breast, and liver cancer in vitro (33,34,42,43). Recently, Li and coworkers demonstrated that inhibition of LDH by oxamate causes a substantial decrease in glucose uptake, lactate production, and significant suppression of nasopharyngeal carcinoma cell proliferation in vitro and in vivo. Only a minimum toxicity to normal nasopharyngeal epithelial cells in vitro was observed (44). Oxamate was also found to be well tolerated in mice (44). In a separate study, oxamate was used to increase cancer sensitivity to Taxol (45).

Applicants hypothesized that a combined use of DCA and oxamate would be more effective in switching glucose metabolism in cancer cells from aerobic glycolysis to oxidative metabolism. The rationale for the combination is that inhibition of LDH by oxamate will lead to a reduction of lactate and accumulation of pyruvate. The accumulated pyruvate, that has been shown to reverse LDH inhibition by oxamate (33,34), will be effectively pushed to mitochondria for oxidative metabolism by DCA through an increased PDH activity. This hypothesis was tested through the use of a human papillomavirus (HPV) positive head and neck squamous cell carcinomas (HNSCCs) mouse model. Applicants' data shows the combination of oxamate and DCA significantly improves the response of the tumor to cisplatin/radiation therapy (CRT) than either of the compounds used alone. CRT is a standard-of-care treatment for the HPV positive HNSCCs in the clinic. The HPV positive HNSCCs mouse model was established in this laboratory and used for the investigation of the effects of lactate on CRT-induced immune-mediated cancer clearance (46).

In addition to the combined use of DCA and oxamate, Applicants have designed prodrugs that use glycerol to connect DCA and oxamate via ester bonds. Applicants' data demonstrates that the prodrugs quickly release DCA and oxamate in mice and improve the response of the tumor to CRT equal to or more effective than the combination of DCA and oxamate.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "prodrug" refers to a compound that undergoes biotransformation before exhibiting pharmacological effects. A prodrug can be a medication that is administered in an inactive or less than fully active form, and which then becomes converted to its active form through a normal metabolic process, such as hydrolysis of an ester form of the drug. Prodrugs are precursor chemical compounds of a drug. In certain embodiments, instead of administering a drug, a prodrug may be used instead to improve how a medicine is absorbed, distributed, metabolized, and excreted (ADME). Prodrugs may be designed to improve bioavailability when a drug itself is poorly absorbed from the gastrointestinal tract. A prodrug may be used to improve how selectively the drug interacts with cells or processes that are not its intended target. This reduces adverse or unintended effects of a drug, especially important in treatments like chemotherapy, which can have severe unintended and undesirable side effects.

As used herein, the phrase "prodrug 1" is used interchangeably with "prodrug AT-N4-001" and "AT-N4-001."

As used herein, the phrase "prodrug 2" is used interchangeably with "prodrug AT-N4-002" and "AT-N4-002."

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The present invention provides intermediates as well as methods of making (e.g., synthetically preparing) compounds of the present invention (e.g., compounds of formula (I)). The compounds of the present invention can be prepared from procedures that are known to those of skill in the art or as shown herein below. Specifically, the compounds of the present invention (e.g., compounds of formula (I)) can be prepared from convenient starting materials, employing procedures (e.g., reagents and reaction conditions) known to those of skill in the art. For example, suitable reagents and reaction conditions are disclosed, e.g., in *Advanced Organic Chemistry, Part B: Reactions and Synthesis*, Second Edition, Carey and Sundberg (1983); *Advanced Organic Chemistry, Reactions, Mechanisms, and Structure*, Second Edition, March (1977); Greene, T. W., *Protecting Groups In Organic Synthesis*, Third Edition, 1999, New York, John Wiley & sons, Inc.; and *Comprehensive Organic Transformations*, Second Edition, Larock (1999). Additionally, specific exemplary procedures are shown in the examples herein below.

Pharmaceutical Formulations

The compounds described herein can be used to prepare therapeutic pharmaceutical compositions. The compounds may be added to the compositions in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 2% to about 60% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compounds may be applied in pure form, e.g., when they are liquids. However, it will generally be desirable to administer the active agent to the skin as a composition or formulation, for example, in combination with a dermatologically acceptable carrier, which may be a solid or a liquid.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m2, conveniently 10 to 750 mg/m2, most conveniently, 50 to 500 mg/m2 of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antitumor agents and have higher potency and/or reduced toxicity as compared to existing compounds for treating tumors.

The invention provides therapeutic methods of treating cancer in an animal, including but not limited to a mammal. The methods generally which involve administering to an animal having cancer an effective amount of a compound or composition described herein. A mammal includes, but is not limited to, a primate, human, rodent, canine, feline, bovine, ovine, equine, swine, caprine, bovine and the like. Cancer refers to any various type of malignant neoplasm. Examples of cancers include, but are not limited to, HPV, HNSCC, colon cancer, breast cancer, melanoma and leukemia. In general as the term is used herein, "cancer" is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the Example as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Experimental Section

A. General Chemistry

Unless otherwise stated, all reactants, reagents and solvents were obtained from commercial sources and used without further purification. $^1$H and $^{13}$C NMR spectra were recorded on a Bruker Varian 400 spectrometer (Bruker Daltonik, Germany) in CDCl$_3$. All $^1$H NMR experiments are reported in δ units, parts per million (ppm) downfield of TMS, and were recorded relative to the residual undeuterated solvent signal (chloroform, 7.26 ppm). Multiplicities are indicated by s (singlet), d (doublet), t (triplet), m (multiplet), and br s (broad singlet). J values are given in Hz. All $^{13}$C NMR spectra were reported in ppm relative to the signals for chloroform (77 ppm). Low resolution mass spectra (LRMS) were obtained from a Thermoquest Finnigan LCQ Deca Mass Spectrometer (Thermo Fisher Scientific Corp., Waltham, Mass.). Flash column chromatography was carried out with Merck silica gel 60 (mesh 230-400) on a Yamazen Dual Channel W-Prep 2XY Flash Chromatography System (Yamazen Corp., Osaka, Japan). Yields were based on purified products and were not optimized. The purity (>98%) of the prodrugs was determined by HPLC analysis on a Beckman Coulter HPLC (System Gold) system equipped with an Apollo C18 column (250 mm×4.6 mm i.d., 5 μm) and a168 photodiode array detector at 210 nm.

B. General Biology

Mouse oropharyngeal epithelial cells (MOEs) were previously internally derived from C57Bl/6 mouse oropharyngeal epithelium retrovirally transduced with the indicated vectors and oncogenes (56). MOEs are routinely internally screened for the presence of cytokeratin and HPV-16 mRNA as means of authentication, and our model HPV+HNSCC line harboring the E6, E7, and mutated H-Ras$^{V12}$ oncogenes (E6/E7/Ras MOEs) is routinely grafted into syngeneic mice for animal studies (46). Cells were maintained in Dulbecco's modified Eagle's medium (DMEM) containing 10% fetal bovine serum and supplemented with 100 U/ml penicillin and 100 μg/ml streptomycin in a humidified incubator with 5% $CO_2$.

Example 1

Design of Prodrugs

Figure 13:
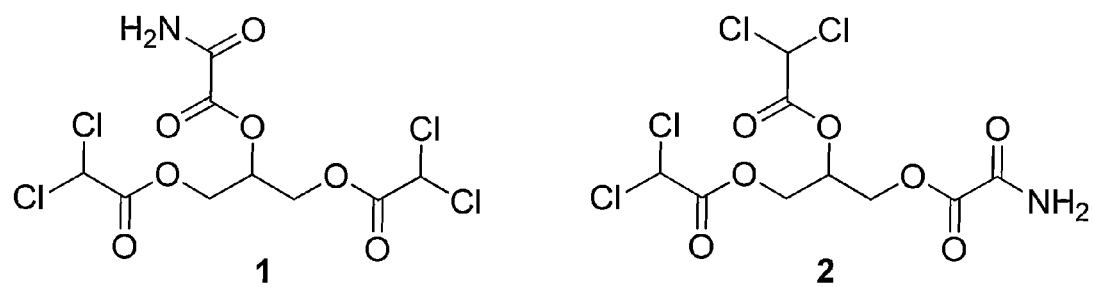
FIG. 13 illustrates the chemical structures of the prodrugs, where 1 is AT-N4-001 and 2 is AT-N4-002.

To design a prodrug of dual inhibition of two enzymes, the $K_i$ value of the inhibitor for each of the targeted enzymes should be comparable so that the inhibition concentration for each targeted enzyme can be achieved once the inhibitor is released from the prodrug. The $K_i$ value of DCA for PDK was reported to be 10-250 μM (26). Although various LDH inhibitors have been developed (35), oxamate was selected for this study due to its comparable $K_i$ value for its targeted enzyme with that of DCA. The $K_i$ value of oxamate for mammalian LDH is 116 μM (47) that makes oxamate ideal to be coupled with DCA in a prodrug for the dual inhibition purpose. Glycerol is selected as a linker to connect DCA and oxamate through ester bonds. Glycerol is an endogenous compound with three hydroxyl groups and has been used as a linker for prodrugs (48-50). Based on $K_i$ values of DCA and oxamate, we decide to couple two molecules of DCA with one molecule of oxamate. Structures of the designed prodrugs are presented in FIG. 13. These two prodrugs were expected to release DCA, oxamate, and glycerol in vivo through the hydrolysis of the ester bonds by esterases.

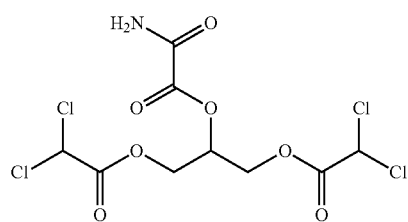

1

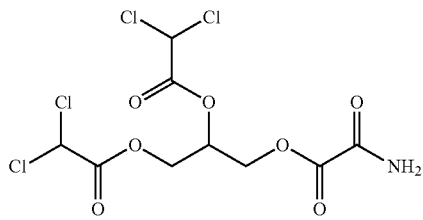

2

Example 2

Synthesis of Prodrugs

Figure 14:
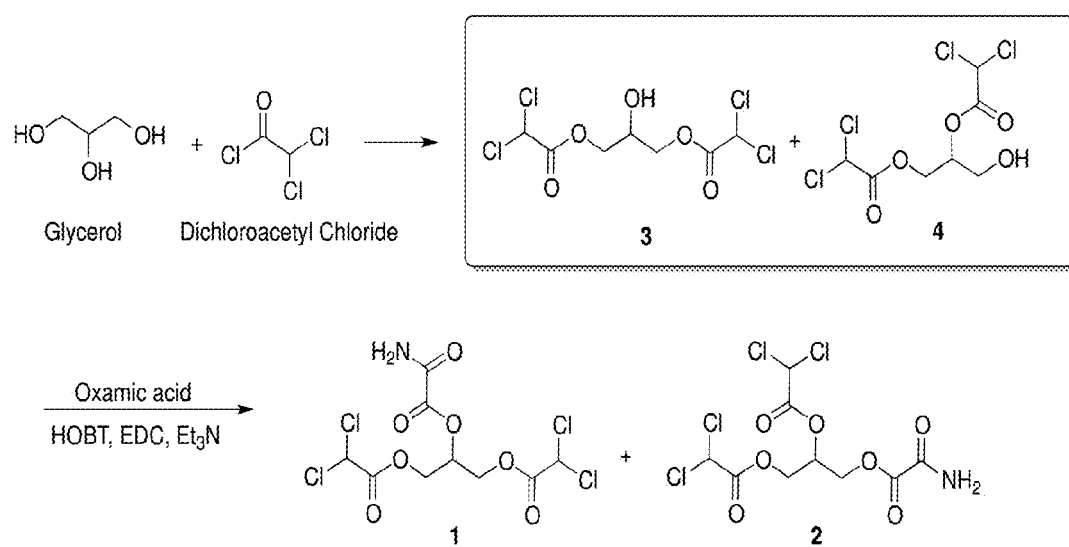
FIG. 14 depicts an outline of the synthesis of prodrugs, where 1 is AT-N4-001 and 2 is AT-N4-002.

The synthetic procedures are outlined in FIG. 14. The synthesis started with esterification of glycerol with dichloroacetyl chloride in the presence of pyridine. The reaction gave a mixture of two constitutional isomers (3, 4) with the second DCA being coupled to a different position (FIG. 14). Without separation, the mixture was subjected to esterification with oxamic acid through the use of 1-hydroxybenzotriazole monohydrate (HOBt) as the carboxylic acid activating agent. Prodrug 1 (1) and prodrug 2 (2) were obtained in 21% and 10% yields respectively. The purity of 1 and 2 was confirmed to be greater than 98% by HPLC.

A) 2-Hydroxypropane-1,3-diyl bis(2,2-dichloroacetate) (3) and 3-hydroxypropane-1,2-diyl bis(2,2-dichloroacetate) (4)

Dichloroacetyl chloride (11.3 mL, 117.2 mmol) was added to a solution of glycerol (5.39 g, 58.6 mmol) in tetrahydrofuran (30 mL) followed by dropwise addition of pyridine (100 μL). The reaction mixture was stirred at room temperature overnight. The organic solvent was removed under reduced pressure. The yellow thick oil residue was diluted with ethyl acetate (150 mL), washed by saturated $K_2CO_3$ solution (100 mL×3), brine (100 mL×2), dried over anhydrous magnesium sulfate, and evaporated under reduced pressure. The obtained residue (16.28 g, yellow oil) was purified by silica gel chromatography (ethyl acetate/hexane 1/6~1/3) to give a mixture of 3 and 4 (8.16 g, 44.6%) as colorless oil. The mixture was used for the next step without further separation.

B) 2-(2-Amino-2-oxoacetoxy)propane-1,3-diyl bis(2,2-dichloroacetate) (1) and 3-(2-amino-2-oxoacetoxy)propane-1,2-diyl bis(2,2-dichloroacetate) (2)

To a solution of the mixture of 3 and 4 obtained above (12.50 g, 39.0 mmol), oxamic acid (3.48 g, 39.0 mmol), 1-hydroxybenzotriazole monohydrate (HOBt-$H_2O$, 5.30 g, 39.0 mmol) and triethylamine (5.42 mL, 39.0 mmol) in DMF (100 ml) was added 1-(3-dimethylaminopropyl)-3-ethylcarbodiimide hydrochloride (EDC-HCl) (7.52 g, 39.0 mmol). The reaction mixture was stirred at room temperature overnight before poured into ice-water (100 mL), extracted with dichloromethane (75 ml×3). The combined organic layer was washed with diluted HCl (pH 2-3, 75 mL×2), saturated $NaHCO_3$ solution (75 mL×2) and brine (75 ml×2), dried over $Na_2SO_4$, and evaporated under reduced pressure. The obtained yellow oily residue was then purified by YFLC to give 1 (AT-N4-001) and 2 (AT-N4-002) respectively as colorless oil, which were then recrystallized in chloroform (5 mL solvent/g crude) to yield 1 (3.12 g, 21.2%) and 2 (1.46 g, 9.73%) as white solid.
1: $^{1}$H-NMR (400 Hz, CDCl$_3$) δ 6.89 (br s, 1H), 6.26 (br s, 1H), 6.00 (s, 3H), 5.54-5.50 (tt, J=6.1, 4.1 Hz, 1H), 4.57 (ddd, J=18.3, 12.2, 5.1 Hz, 4H); $^{13}$C-NMR (400 Hz, CDCl$_3$) δ 164.14, 157.51, 64.67, 62.86; ESI-MS 408 (M+Na)$^+$.
2: $^{1}$H-NMR δ 6.88 (br s, 1H), 5.99 (d, J=5.84 Hz, 2H), 5.86 (br s, 1H), 5.53–5.48 (tt, J=5.9, 4.1 Hz, 1H), 4.67–4.49 (m, 4H); $^{13}$C-NMR (400 Hz, CDCl$_3$) δ 164.20, 163.99, 157.94, 72.27, 64.72, 62.92; ESI-MS 386 (M+H)$^+$.
C) Prodrug Synthesis Scheme 1
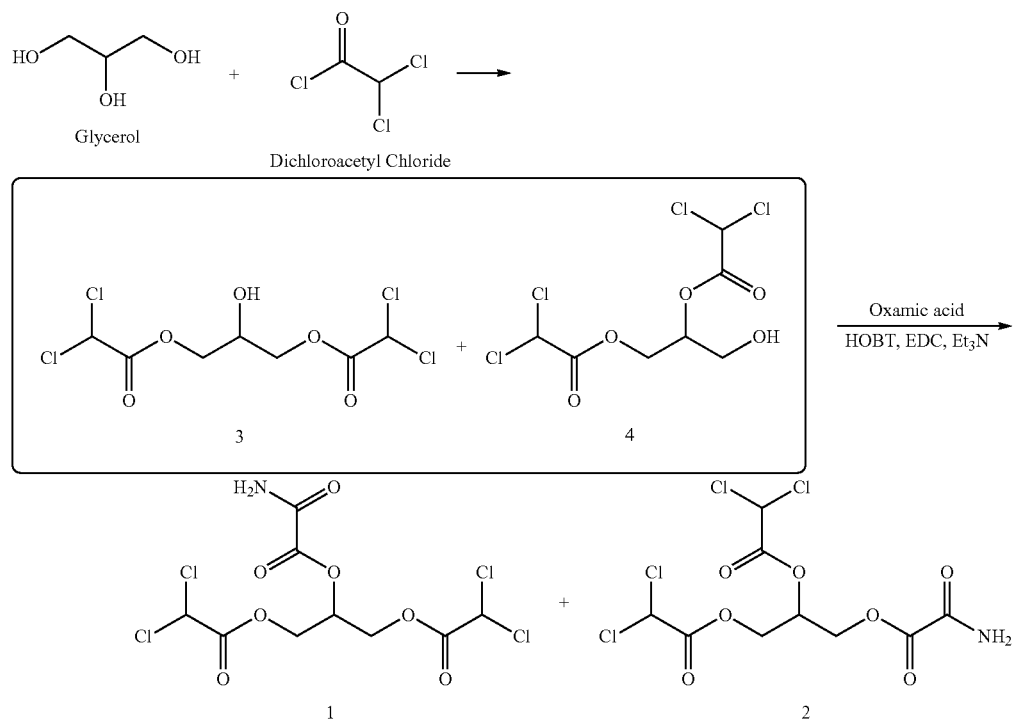
D) Prodrug Synthesis Scheme 2
Prodrugs of DCA (AT-25, AT-32 and the mixture of AT-23-a and AT-23-b) can be synthesized as follows:
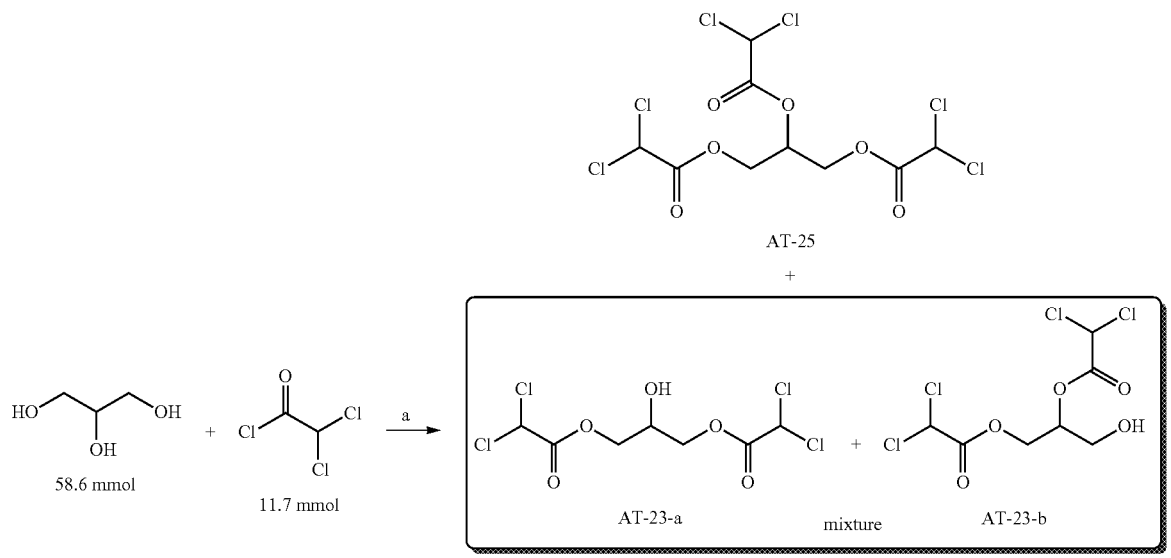

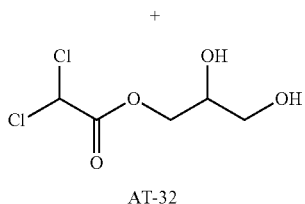

AT-32 a. Tetrahydrofuran (THF) 30 mL, room temperature, overnight

A representative example for synthesizing the prodrugs of the invention is provided above in Scheme 2. In one embodiment, the synthesis is accomplished by combining 58.6 mmol of oxamic acid sodium salt with 11.7 mmol dichloroacetic acid sodium salt, adding 30 mL tetrahydrofuran (THF) to the mixture and allowing the mixture to react at room temperature, overnight. The resulting prodrugs are AT-25, a mixture of AT-23-a and AT-23-b, and AT-32.

E) Prodrug Synthesis Scheme 3

Prodrugs AT-N4-001 and AT-N4-002 can be synthesized as follows:

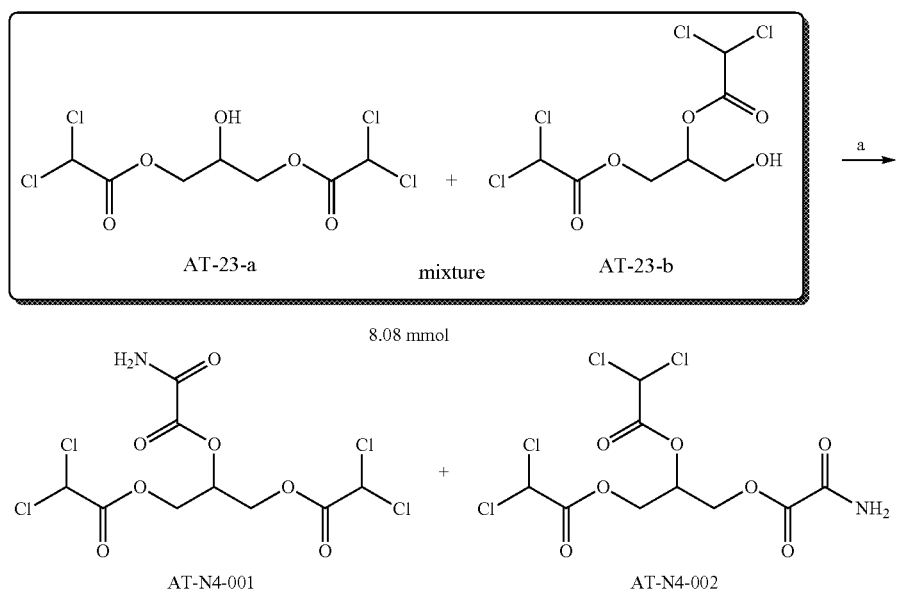

a. Oxamic acid (8.08 mmol), 1-hydroxybenzotriazole monohydrate (HOBt—H2O, 8.08 mmol), triethylamine (8.08 mmol) 1-(3-dimethylaminopropyl)-3-ethylcarbodiimide hydrochloride (8.08 mmol) in DMF (100 mL), room temperature, overnight A representative example for synthesizing the prodrugs of the invention is provided above in D). In one embodiment, the synthesis is accomplished by combining 8.08 mmol of AT-23-a and AT-23-b. The resulting prodrugs are AT-N4-001 and AT-N4-002.

Example 3

Chemical and Metabolic Stability of Prodrugs 1 and 2

Figure 15:
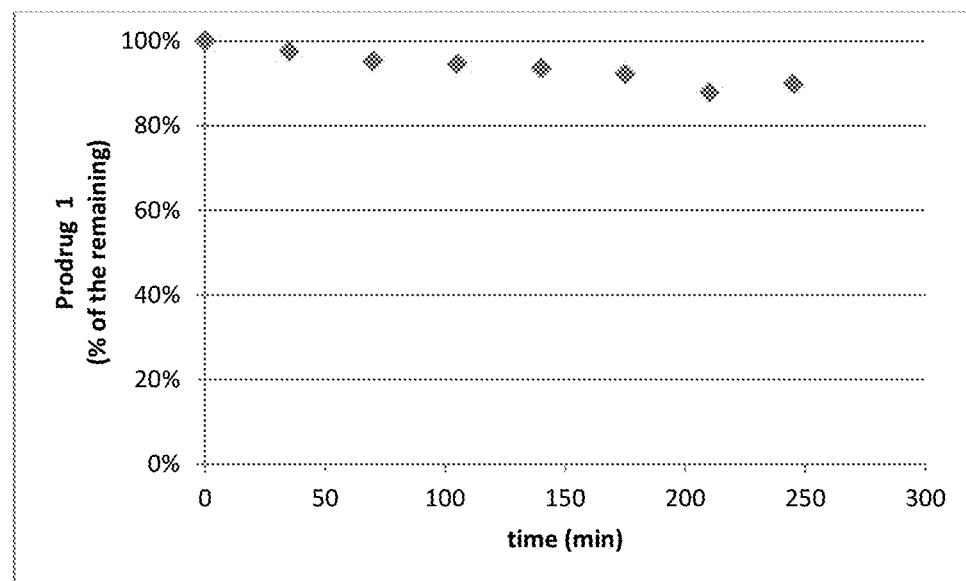
FIG. 15 provides a graph of the hydrolysis of prodrug 1 (FIG. 15A) and prodrug 2 (FIG. 15B) in aqueous acetonitrile solution. Prodrug 1 or prodrug 2 (0.42 mg/mL) in aqueous acetonitrile (H2O:CH3CN=1:1) was stirred at ambient temperature. Aliquots were withdrawn and analyzed for the prodrug by HPLC as described in the experimental section.
Figure 15:
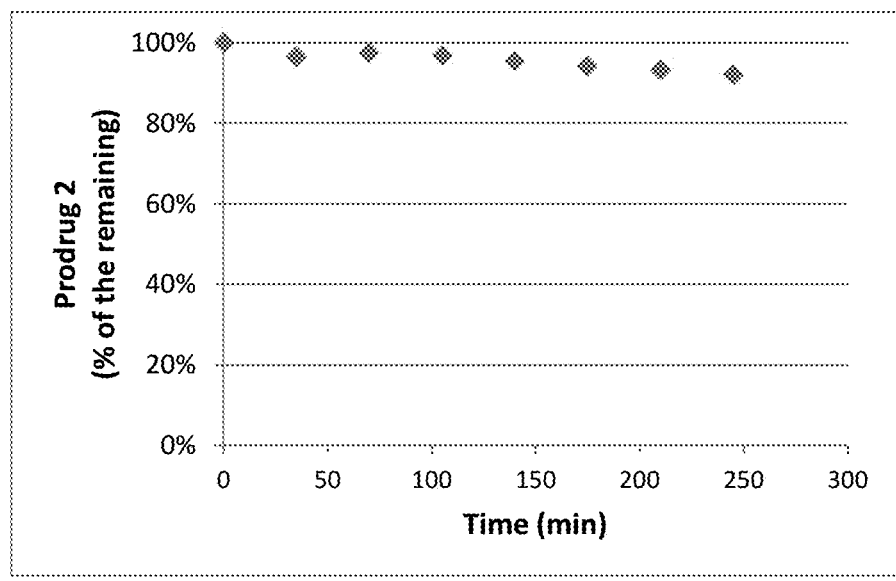

Once the two prodrugs were obtained, their chemical stability and metabolic stability were determined. The chemical stability of prodrug 1 and prodrug 2 was determined in aqueous acetonitrile at ambient temperature. The prodrug (0.4 mg/mL) a mixture of water and acetonitrile (1:1) at ambient temperature. Aliquots were taken from the solution periodically and checked by HPLC for the presence of the prodrug. The HPLC analysis was carried out on a Beckman Coulter HPLC (System Gold) system, controlled by a system controller (32 Karat workstation with PC), equipped with a 125 gradient pumping module, a 508 autosampler with a sample cooling system, and a 168 photodiode array detector. The HPLC conditions employed an Apollo C18 column (250 mm×4.6 mm i.d., 5 μm) (Alltech, Deerfield, Ill.) and aqueous acetonitrile (50% with 0.1% TFA) as the mobile phase. The flow rate was 0.8 mL/min and the detection wavelength was 210 nm. Under the condition, the retention time for prodrugs 1 and 2 was 9.83 and 9.87 minutes respectively. Applicants' data demonstrates that both prodrug 1 and 2 underwent about 10% hydrolysis in 4 hours. FIG. 15 provides a representative plot of the remaining prodrug (prodrug 1 or prodrug 2) against the time.

In vivo release of the prodrugs was investigated with female C57BL/6 mice. Mice were housed four in a cage and received food and water ad libitum. All mice were used at approximately 7-10 weeks of age and given at least one week break after arrival. All experimental protocols were approved by the Institutional Animal Care and Use Committee at South Dakota State University. A prodrug (1 or 2), suspended in 3% (v/v) Tween 80 in saline (30.4 mg/ml), was administered (7.6 mg/mouse) to mice by i.p. Blood samples were obtained through retro-orbital bleeding with mice under general anesthesia through the use of isoflurane. The blood samples were immediately frozen in liquid nitrogen and stored at −80° C. freezer before LC/MS/MS analysis.

The blood sample was quickly thawed at 37° C. The sample (200 µl) was first mixed with acetonitrile (200 µm) and centrifuged at 14000 rpm for 2 min at 4° C. The precipitates were washed with additional acetonitrile (2×200 µl) and centrifuged. The combined supernatant was filtered through a 0.2 mm syringe filter and immediately subjected to LC/MS analysis.

LC/MS/MS analysis was completed on a ThermoFinnigan TSQ Quantum Ultra triple quadrupole mass spectrometer coupled with an Agilent Eclipse XDB-C18 column (2.1-150 mm, 5 µm) equipped with an Agilent XDB-C8 guard column. The mobile phase was composed of 6 mM ammonium acetate and acetonitrile at a ratio of 50/50 (v/v). The flow rate was set at 70 µL/min. For samples derived from mice dosed with prodrug 1, the electrospray ion source was operated in the negative ionization mode for four minutes to detect DCA and oxamate before switched to the positive ionization mode to detect prodrug 1. Selected reaction monitoring (SRM) was performed to monitor the mass transition of 386→97 (prodrug 1), 127→83 (DCA) and selected ion monitoring (SIM) was performed to monitor oxamate at the m/z of 88.0. For samples derived from mice dosed with prodrug 2, all the parameters were the same as set for prodrug 1 except the electrospray ion source was operated in the negative ionization mode for all the analytes. Prodrug 2 was detected by monitoring the mass transition of 384→126.

Figure 16:
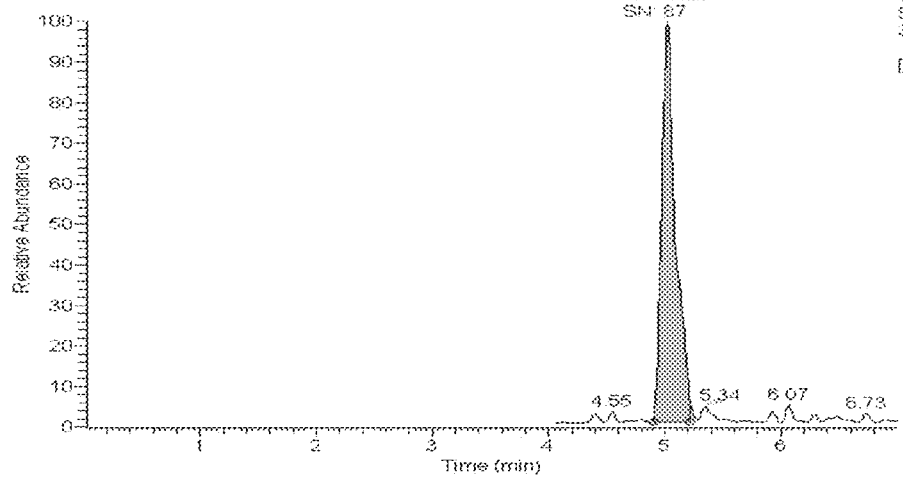
FIG. 16 provides LC/MS chromatograms derived from blood samples of mice dosed with prodrug 1 (AT-N4-001) (A). Mice were dosed with prodrug 1 (7.6 mg/mouse) by i.p. Blood samples were collected at 5 min and 25 min for mice dosed with prodrug 1 through retro-orbital bleeding with mice under general anesthesia. After protein precipitation by acetonitrile, samples were analyzed by LC/MS/MS. For samples derived from mice dosed with prodrug 1, the electrospray ion source was operated in the negative ionization mode for four minutes to detect DCA and oxamate before switched to the positive ionization mode to detect prodrug 1. Selected reaction monitoring (SRM) was performed to monitor the mass transition of 386→297 (1), 127→83 (DCA) and selected ion monitoring (SIM) was performed to monitor oxamate at the m/z of 88.0.
Figure 16:
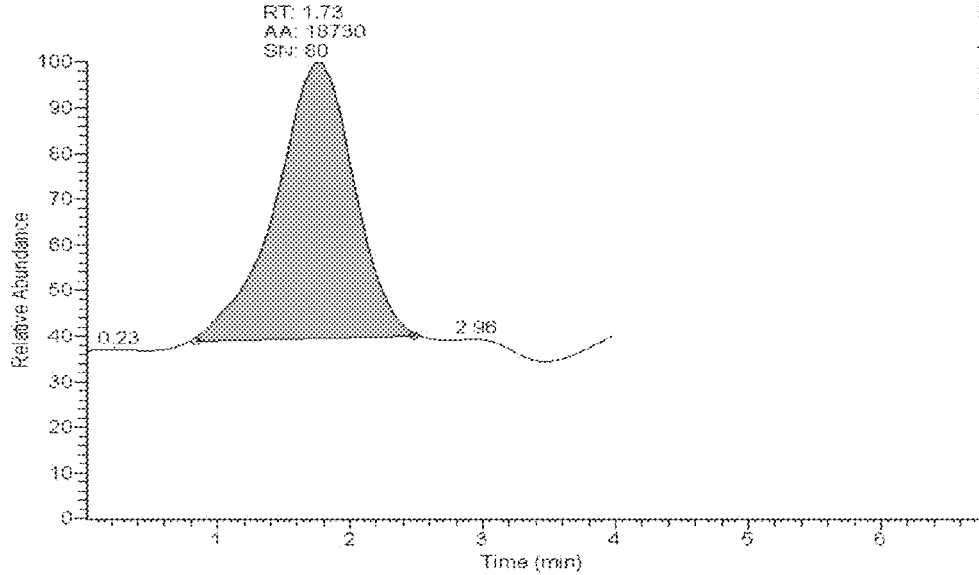
Figure 16:
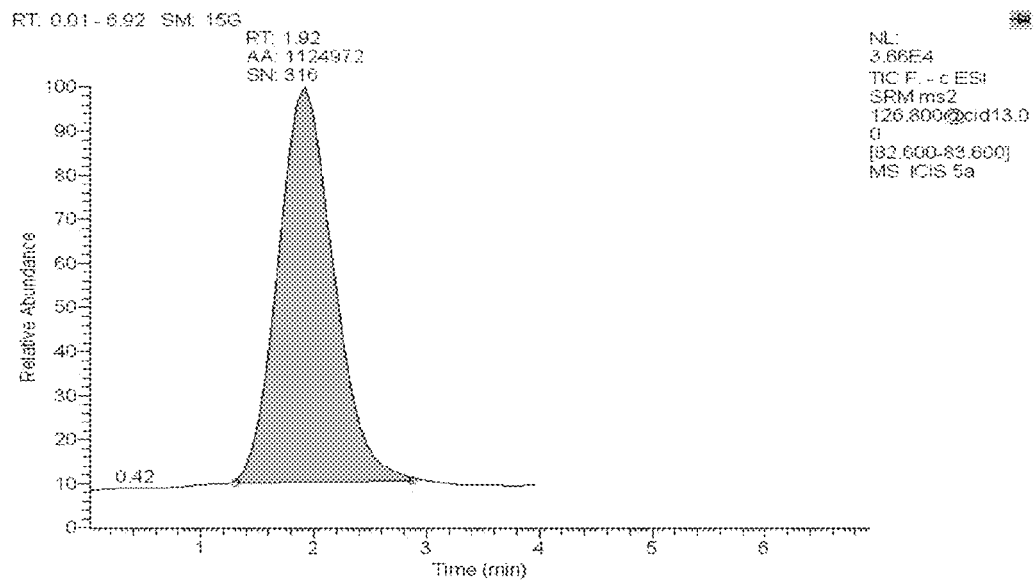
Figure 16:
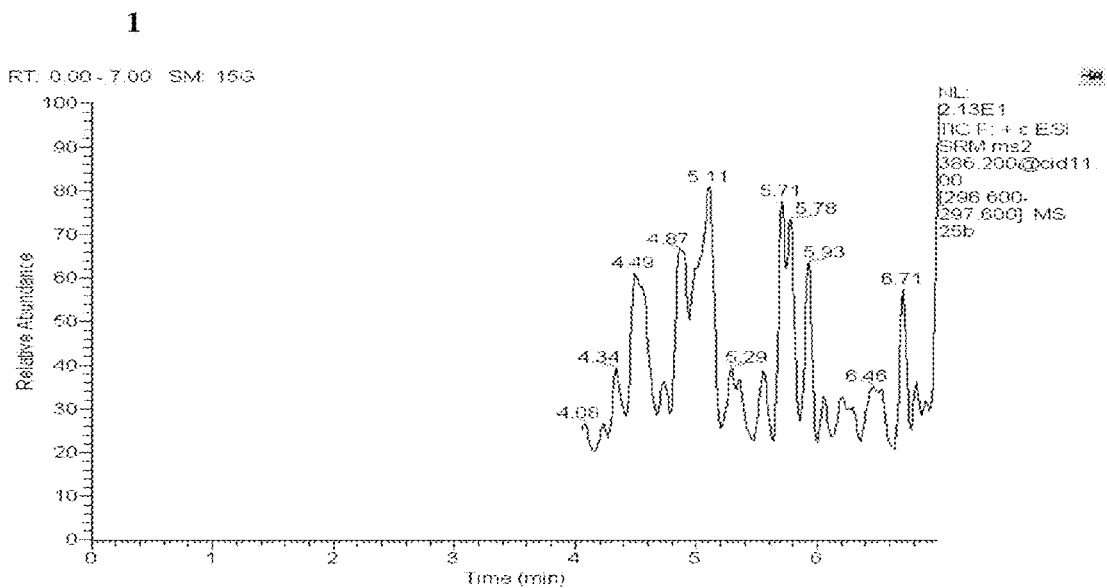
Figure 16:
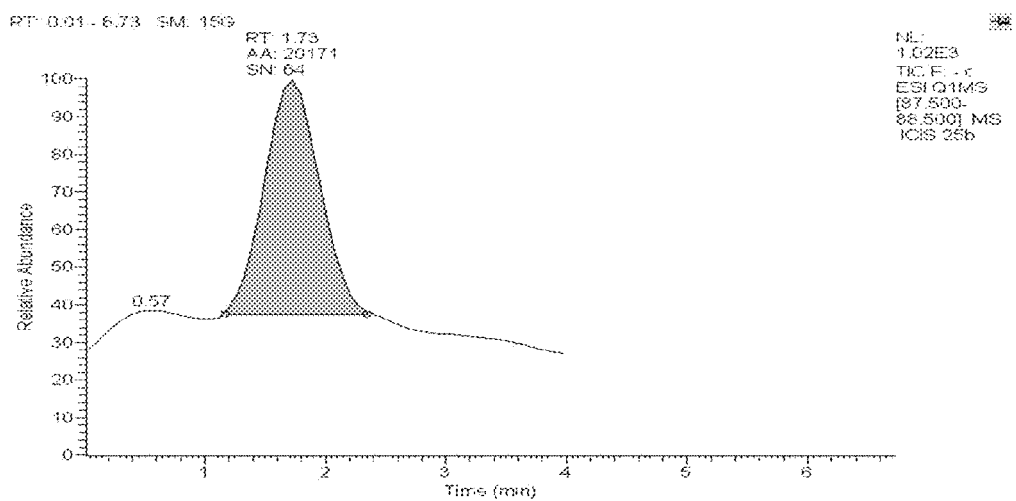
Figure 16:
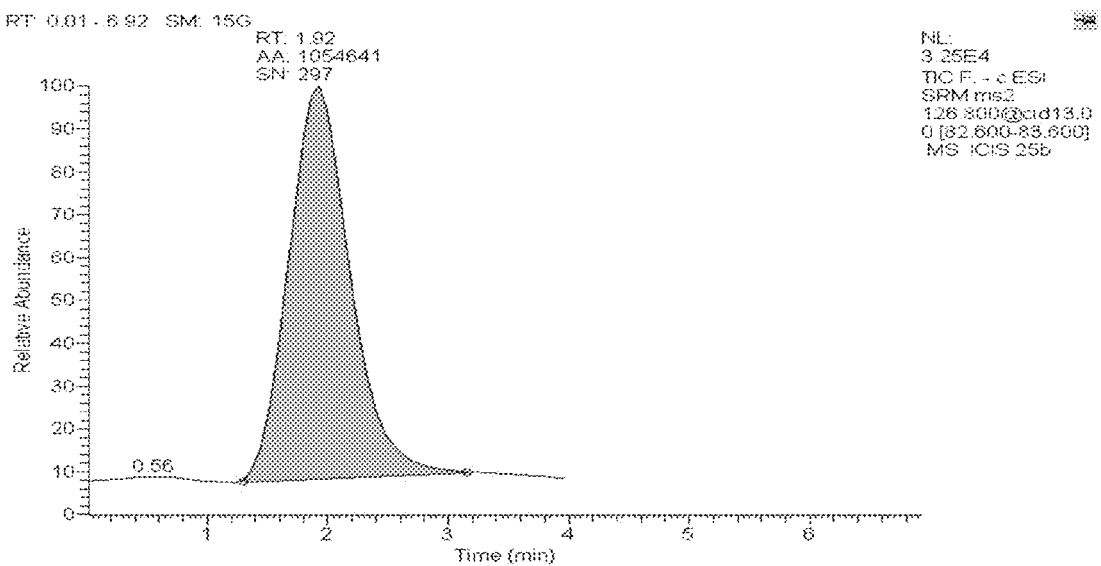
Figure 17:
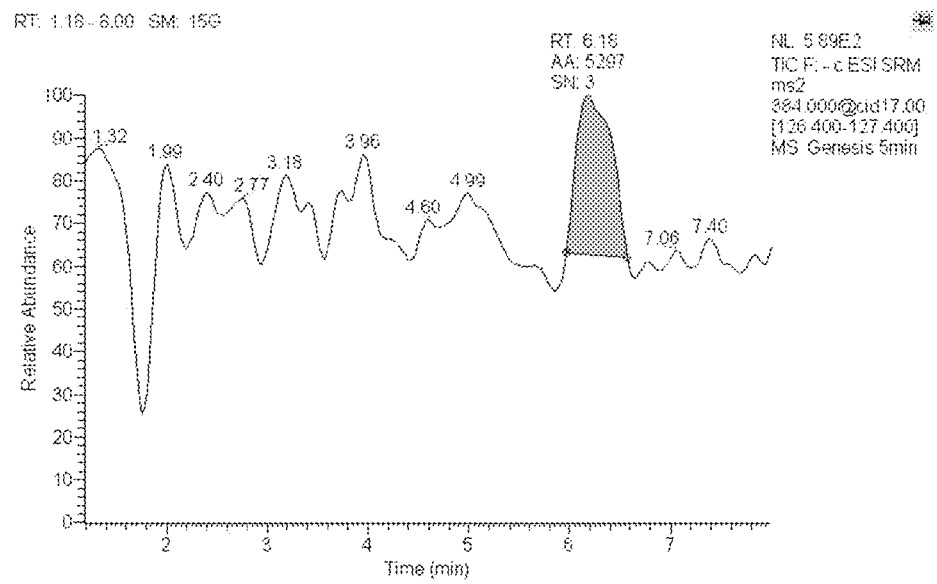
FIG. 17 provides LC/MS chromatograms derived from blood samples of mice dosed with prodrug 2 (AT-N4-002) (B). Mice were dosed with prodrug 2 (7.6 mg/mouse) by i.p. Blood samples were collected at 5 min and 30 min for a mouse dosed with prodrug 2 through retro-orbital bleeding with mice under general anesthesia. After protein precipitation by acetonitrile, samples were analyzed by LC/MS/MS. For samples derived from mice dosed with prodrug 2, all the parameters were the same as set for prodrug 1 except the electrospray ion source was operated in the negative ionization mode for all the analytes. Prodrug 2 was detected by monitoring the mass transition of 384→126.
Figure 17:
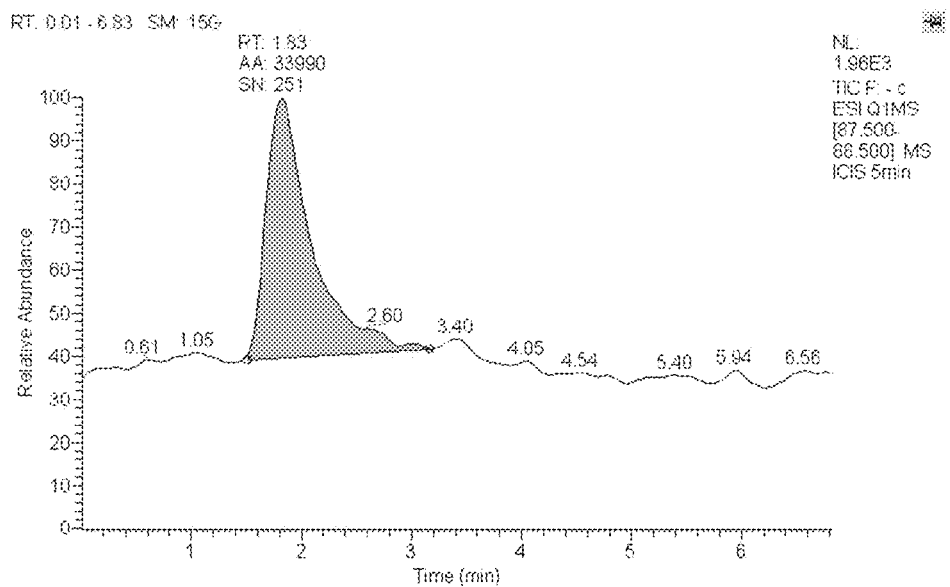
Figure 17:
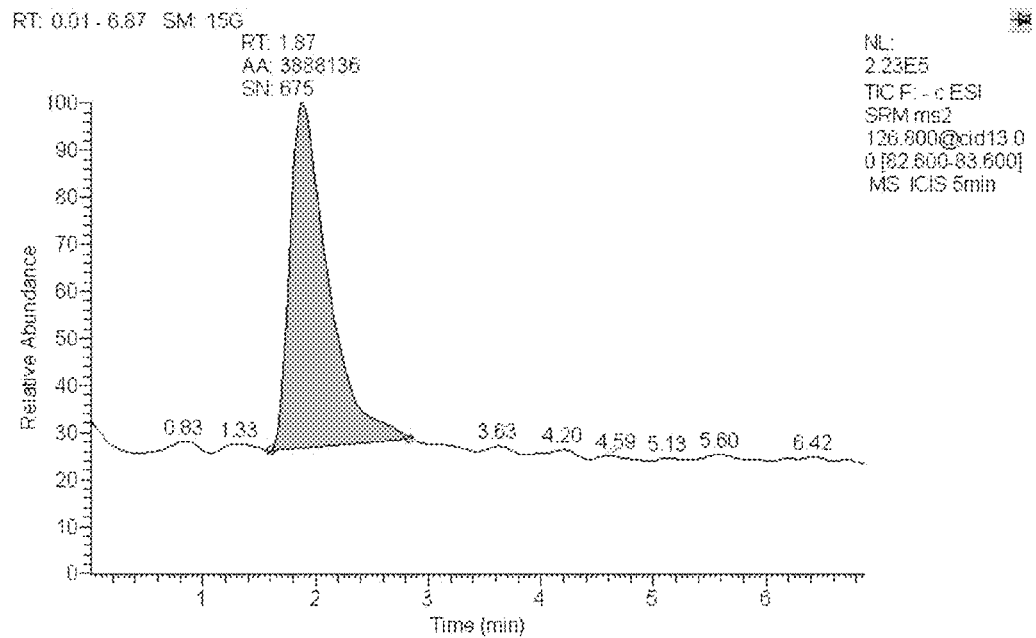
Figure 17:
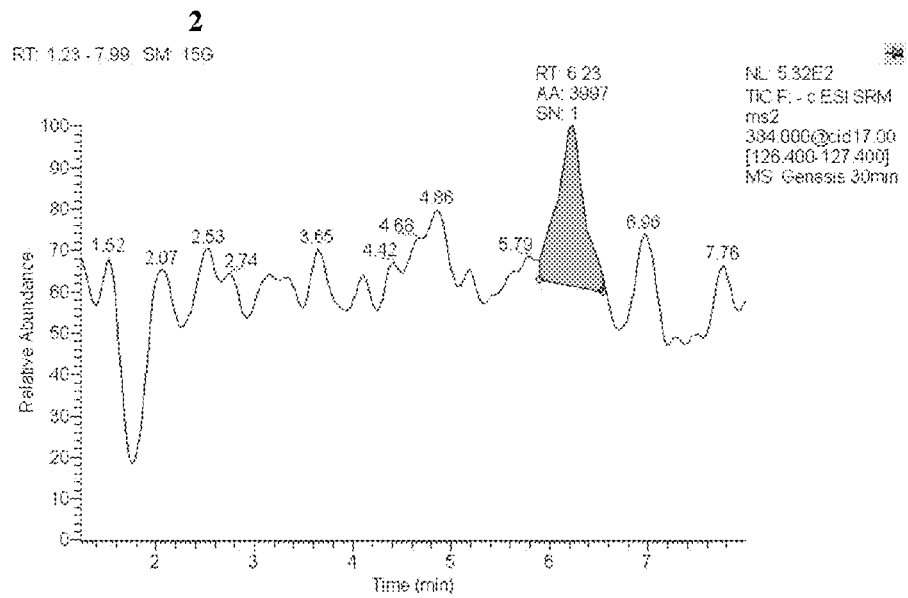
Figure 17:
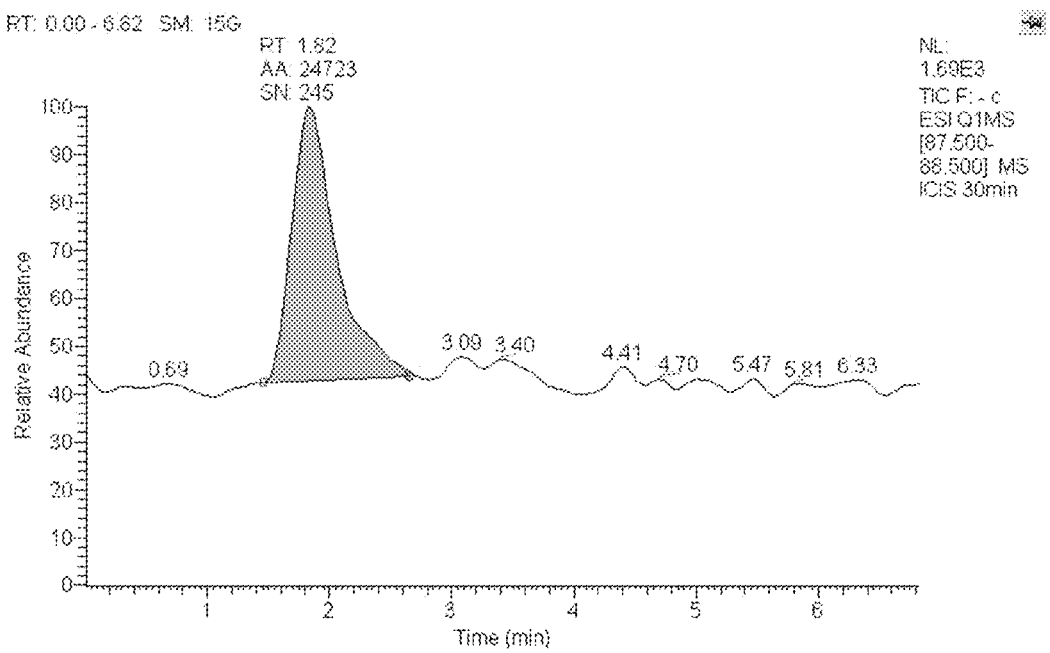
Figure 17:
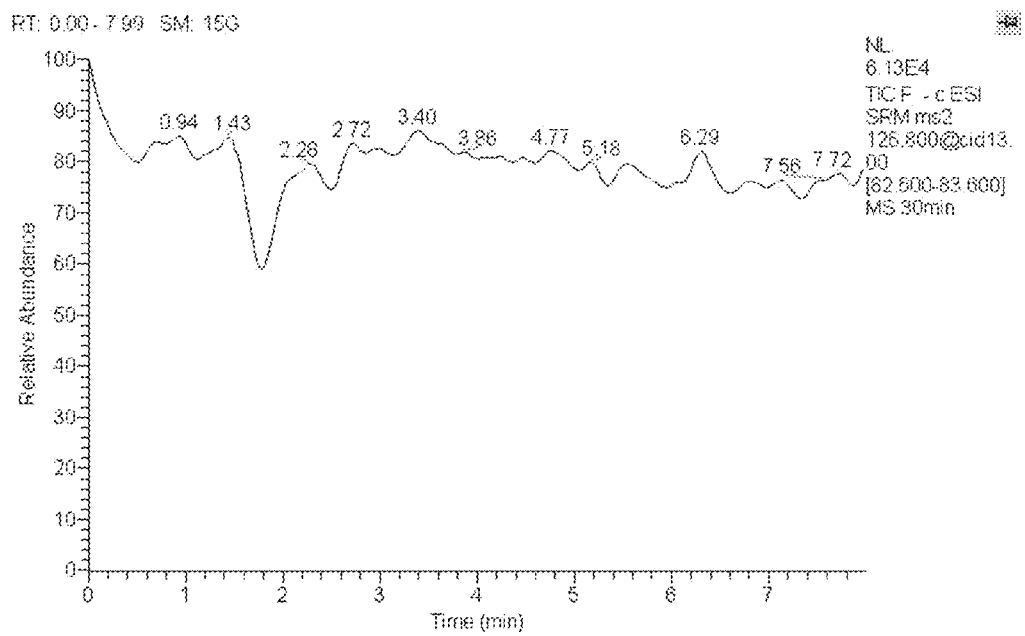

When given to female C57BL/6 mice by i.p. (7.6 mg/mouse), both AT-N4-001 and AT-N4-002 quickly released DCA and oxamate. As demonstrated in FIGS. 16 and 17, when the prodrugs were given by i.p., significant DCA and oxamate were detected in the blood samples within 5 minutes. No prodrug was detected after 25 min (for 1) or 30 min (for 2) in the blood samples (FIGS. 16 and 17). These data confirm that 1 and 2 are effective prodrugs of the combination of DCA and oxamate.

Example 4

The Effect of DCA, Oxamate, DCA+Oxamate, Prodrug 1 and Prodrug 2 on Tumor Responses to Cisplatin/Radiation Therapy (CRT)

The effects of various treatments on tumor responses were carried out by examining whether the treatment could improve tumor's response to CRT with a HPV positive HNSCCs mouse model. CRT is a standard treatment for HPV-positive HNSCC in the clinic (46). Selection of HPV positive HNSCCs mouse model for the investigation was based on the fact that LDH was highly expressed in head and neck cancer cells and was found to be associated with local relapse, worse survival and distant metastasis (51). Applicants also used this model to investigate the effects of lactate on CRT-induced immune-mediated cancer clearance (46) and DCA's effect on the tumor's response to CRT (unpublished data). The literature reported dosages of DCA and oxamate were used (6,23,52,53)(41).

Figure 18:
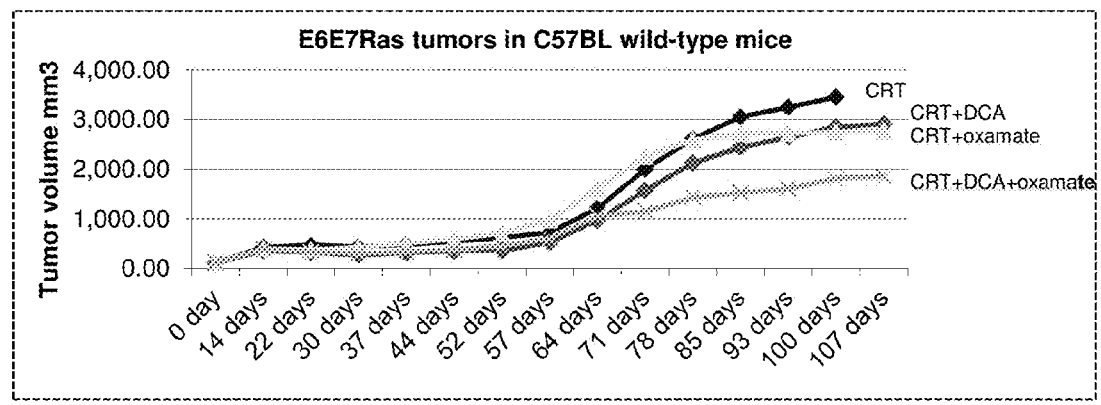
FIG. 18. The effects of DCA, oxamate, DCA plus oxamate on the responses of HPV+E6E7 Ras tumor to CRT. One million E6/E7/Ras MOEs cells were injected subcutaneously into the rear leg of wild-type C57Bl/6 mice. After 11 days, a treatment with DCA (6 mg/mouse) and oxamate (15 mg/mouse) were injected daily by i.p. on weekdays for the remainder of the experiment. All mice received three rounds of treatment with CRT (0.132 mg/mouse cisplatin and 8 Gy radiation, weekly starting at day 11). Tumor volume is $mm^3$.
Figure 19:
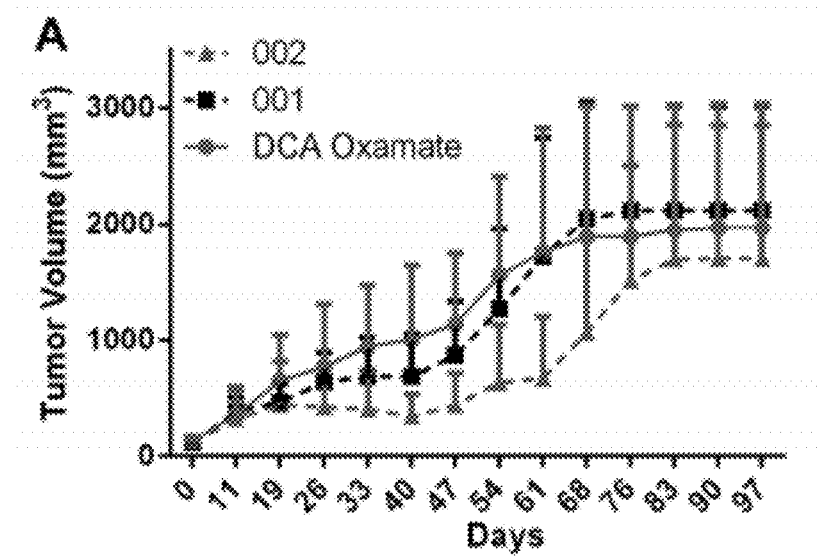
FIG. 19 depicts the effects of DCA plus oxamate vs the effects of prodrug 1 or prodrug 2 on the responses of HPV+E6E7 Ras tumor to CRT. Tumors were initiated by injecting $0.5 \times 10^6$ E6/E7/Ras MOEs cells. After 11 days, a treatment with DCA (6 mg/mouse) plus oxamate (2 mg/mouse), or prodrug 1 (7.6 mg/mouse), or prodrug 2 (7.6 mg/mouse) was initiated daily by i.p. on weekdays. The doses of DCA and oxamate were equal molar equivalents as would be released from the prodrugs. All mice received three rounds of treatment with CRT (0.132 mg/mouse cisplatin and 8 Gy radiation, weekly starting at day 11). Tumor volume is in $mm^3$.

The effects of DCA, oxamate or DCA+oxamate on tumor's response to CRT were examined first. As showed in FIG. 18, both DCA and oxamate alone improved tumor's response to CRT. DCA appears to be more effective than oxamate. When DCA and oxamate were used together, the tumor's response to CRT was significantly further improved (FIG. 18). The data confirm that DCA and oxamate is an effective drug combination in sensitizing tumor's response to CRT.

Figure 8:
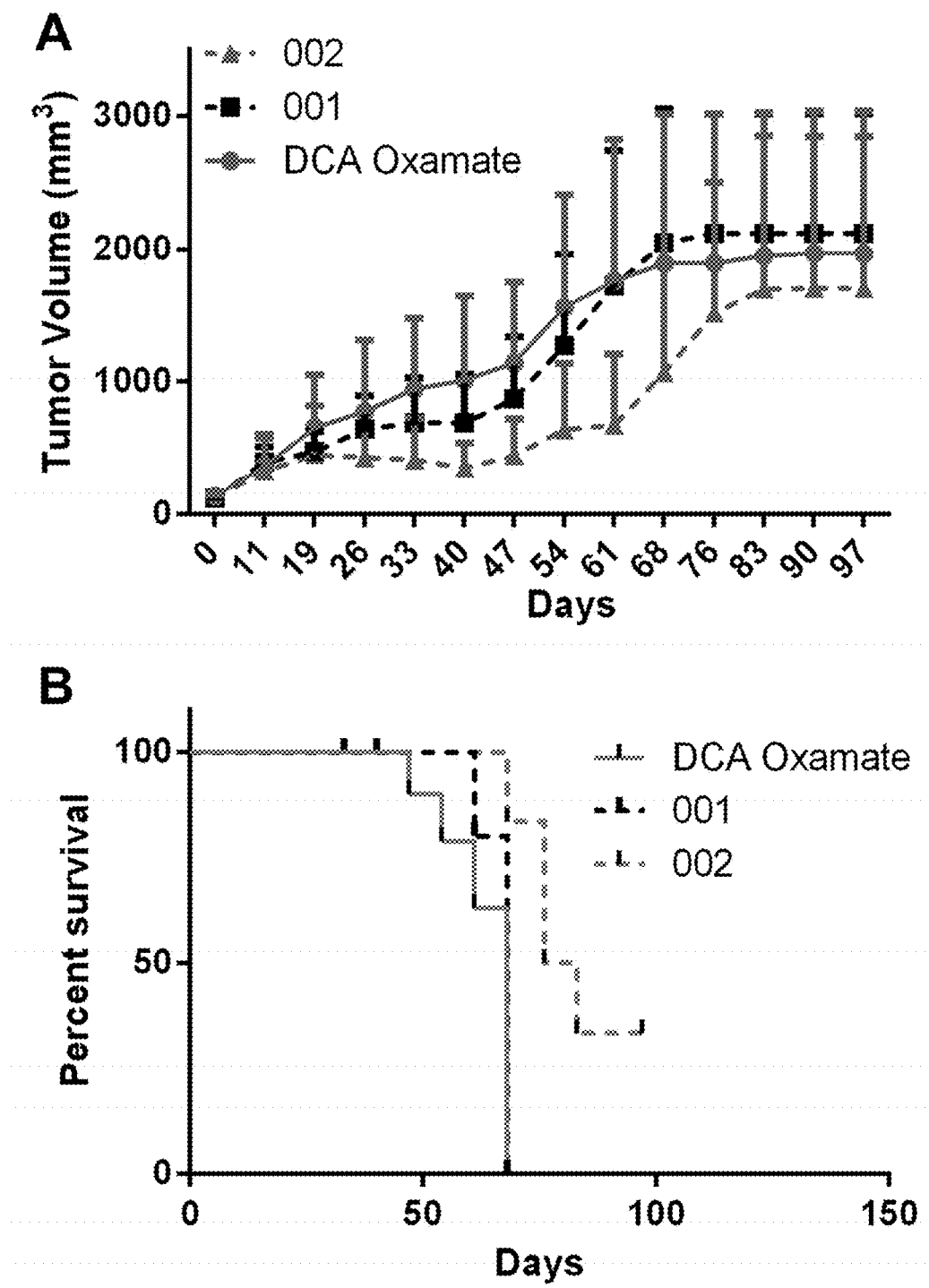
FIG. 8 illustrates a comparison of prodrugs to DCA plus oxamate on tumor growth (A) or on survival (B) with HPV+ model of HNSCC in wild-type C57Bl/6 mice. All mice received 3 rounds of CRT [cisplatin (0.132 mg/mouse) plus radiation (8 Gy/mouse) treatment (Tx) at weekly intervals starting 11 days after tumor initiation]. Mice receiving DCA (6 mg/mouse) plus oxamate (2.2 mg/mouse) were treated every weekday starting with the first chemoradiation treatment by i.p. injection. Mice treated with AT-N4-001 or AT-N4-002 prodrugs (7.6 mg/mouse) were treated on the same schedule as mice treated with DCA+oxamate.

We then conducted an experiment to compare the effects of DCA plus oxamate with the effects of the prodrugs. In this experiment DCA and oxamate were given at equal molar ratios that are expected to be released by the prodrugs. Accordingly, dosage of DCA (6 mg/mouse/day) was the same as that given in FIG. 18 but the dosage of oxamate (2 mg/mouse/day) was lower than that given in FIG. 18. FIG. 8 represents the data from the experiment. The data revealed that prodrug 1 was about equally potent as that of the combination although it appeared to be more effective in the early stage but the trend was not maintained over longer times. Prodrug 2 was more effective than DCA plus oxamate during the entire experiment. In a separate in vivo experiment, Applicants found that prodrug 2 was more effective in reducing lactate production and acidity in tumor tissues than DCA plus oxamate (data not shown). Various factors might contribute to this enhanced activity, such as prodrug 2 itself might be active or the prodrug might have more favorable pharmacokinetics in producing the effects, such as better distribution in mitochondria where one of the targeted enzymes is located. Pathak and co-workers noted that DCA's distribution in mitochondria was poor despite its excellent oral bioavailability. The team addressed this issue by coupling a lipophilic triphenylphosphonium cation to DCA through a biodegradable linker. The resulted molecule Mito-DCA effectively delivered DCA to mitochondria, caused a switch of cancer cells from glycolysis to glucose oxidative metabolism, and subsequent cell death via apoptosis without any significant effects on normal cells (54). The reduction of lactate caused by Mito-DCA was also coupled with an increase in anti-tumor immune responses thus introducing the concept of combining glycolysis inhibition with immune system to destroy tumor (54). Other formulation of DCA (DCA and diisopropylamine dichloroacetate) was also reported (55). Nevertheless, further investigation is needed to identify the factors that contribute to the improved activity of prodrug 2.

Example 5

In Vivo Tumor Growth Inhibition

To study the effects of the prodrugs on tumor growth in vivo, C57Bl/6 immune-competent mice implanted with E6/E7/Ras MOEs cells were used as described previously (46). All experiments were performed in accordance with institutional and national guidelines and regulations with the protocol approved by the Animal Care and Use Committee at Sanford Research. Briefly, $1\times10^6$ tumor HPV+HNSCC cells were injected into the right subcutaneous flank of syngeneic male C57Bl/6 mice. Eleven days after tumor initiation, treatment was initiated daily on weekdays by i.p. injection of vehicle, DCA, Oxamate, DCA+oxamate, prodrug 1, or prodrug 2. All mice received three rounds of treatment with cisplatin/radiation therapy (CRT: 0.132 mg/mouse cisplatin and 8 Gy radiation, weekly starting at day 11). Tumor dimensions were measured weekly to monitor growth. Mice with tumors reaching a volume of 3000 $mm^3$ or becoming substantially emaciated were euthanized.

Example 6

Figure 4:
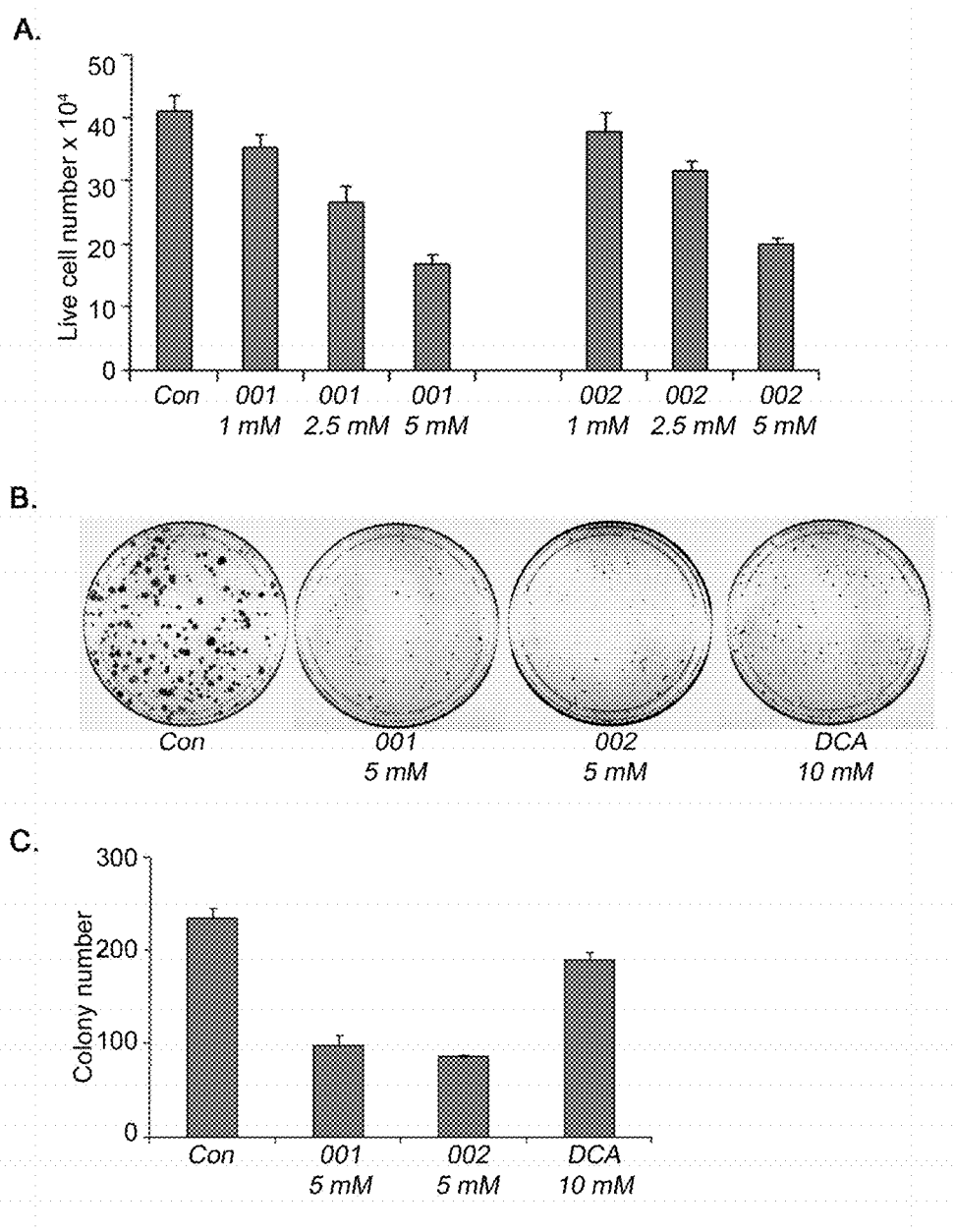
FIG. 4 illustrates prodrugs AT-N4-001 and AT-N4-002 inhibiting cell proliferation and colony growth of E6E7/Ras MTE cells. (A) E6E7/Ras MTE cultures were treated with DMSO (Con), AT-N4-001, or AT-N4-DCA 002 at the indicated concentration for one day. Live cell number was then determined using a trypan blue exclusion assay. (B) E6E7/Ras MTE cells were seeded on 100-mm plate at 500 cells per plate (in triplicate). After one day, cells were treated as indicated and allowed to grow until colonies of untreated controls reached 50 or more cells (7 days). Plates were stained with Coomassie blue to visualize the colonies. (C) Quantification of colonies described in B. Colonies with more than 15 cells were counted.

Compounds AT-N4-001 and AT-N4-002 Reduce Cell Proliferation and Colony Formation in E6E7/Ras MTE Cells E6E7/Ras MTE cells are mouse tonsilar epithelial cells that have been transformed by HPV oncogenes E6 and E7 together with activated ras. They form tumors in mice and are a model of human HPV+HNSCC. These cells were treated in culture with either vehicle control (DMSO), AT-N4-001, or AT-N4-002 at concentrations of 1 mM, 2.5 mM and 5 mM for one day. Live cells were counted using a hemocytometer (FIG. 4A). With increasing concentrations of AT-N4-001 or AT-N4-002 there are significant reductions in live cell number, indicating that these compounds interfere with proliferation or survival of E6E7/Ras MTE cells. The effects of the compounds on clonogenic growth of the cells were also tested. E6/E7/Ras MTE cells were seeded in 100 mm plates in triplicate, and the next day cells were treated with either vehicle control DMSO, 5 mM AT-N4-001, 5 mM AT-N4-002, or 10 mM DCA. DCA was used at a twice the concentration because the prodrugs each carry two molecules of DCA. FIG. 4B shows an image of the typical colony size and number for each treatment group. AT-N4-001, AT-N4-002, and DCA all promote approximately equal reductions in colony size. However, the number of colonies was significantly lower in the prodrug treated cultures than in the DCA treated cultures (FIG. 4C). This suggests the prodrugs have effects on cell survival and that the inclusion of oxamate in the compounds may have important consequences.

Example 7

Figure 5:
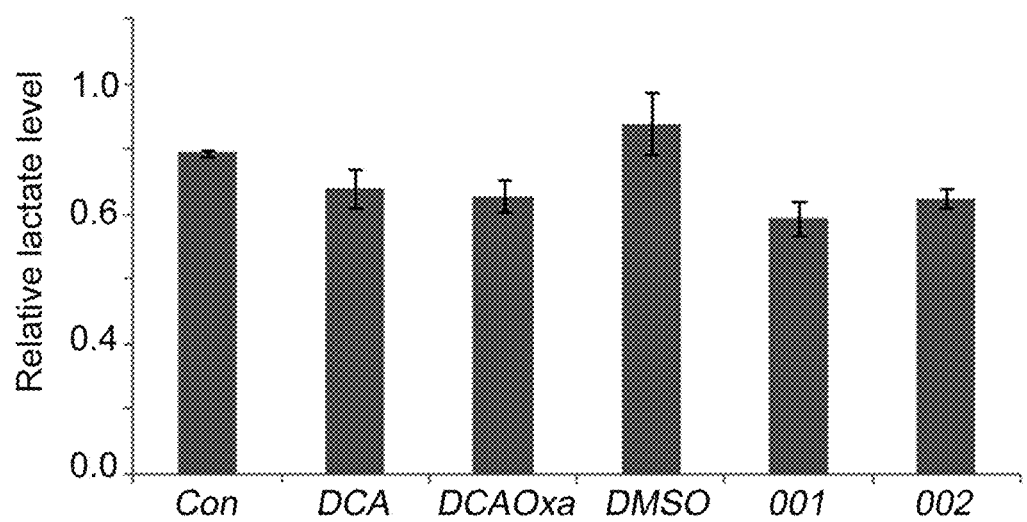
FIG. 5 illustrates the reduction of lactate secretion in cultured cells by prodrugs AT-N4-001 and AT-N4-002. E6E7Ras cells were plated in 100 mm dishes and grown to confluence. The medium was changed to bicarbonate-free DMEM-10% FBS with or without the indicated treatments (5 mM each). Four hours later the medium was collected and lactate was measured using an enzyme based assay from Eton Bioscience. Con indicates the control samples for the DCA and Oxamate samples. DMSO indicates the vehicle only control for the AT-N4-001 and AT-N4-002 prodrug samples.
Figure 6:
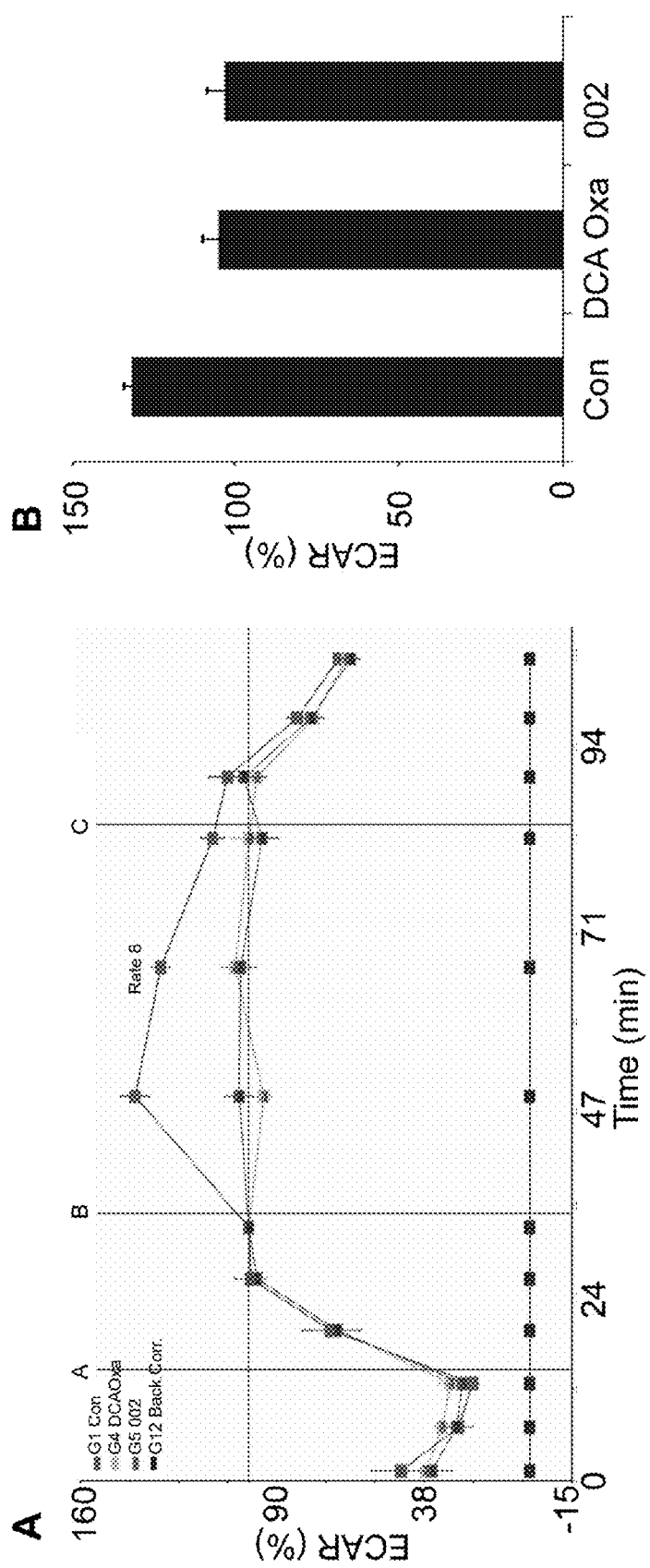
FIG. 6 illustrates the reduction of extracellular acidification rate (ECAR) by prodrugs AT-N4-001 and AT-N4-002. (A) ECAR was measured using a Seahorse XF24 instrument. At time point A glucose was added to the cultures. At time point B the indicated drugs were added with additional glucose. At time point C 2-deoxyglucose was added to block glycolysis. (B) Bar graph of ECAR at the time point indicated as Rate 8 in A.

Compounds AT-N4-001 and AT-N4-002 Reduce Lactate Production Through Glycolysis AT-N4-001 and AT-N4-002 should each release two molecules of DCA and one molecule of oxamate. Both DCA and oxamate are expected to reduce cellular lactate production. Therefore, we examined the changes in lactate after treatment of E6E7/Ras cells with the prodrugs. E6E7/Ras cells were seeded into 100 mm dishes and the next day treated with 5 mM AT-N4-001, 5 mM AT-N4-002, 5 mM DCA plus 5 mM oxamate, or 5 mM DCA alone. Culture medium was collected after 4 hours of treatment and lactate levels were determined (FIG. 5). Both AT-N4-001 and AT-N4-002 significantly reduce lactate production by the cells. The combination of DCA and oxamate or DCA alone also reduces lactate production but to a lesser extent than the prodrugs. To confirm the effects of these compounds on lactate production, the extra cellular acidification rate (ECAR) was measured using a Seahorse XF24 Extracellular Flux analyzer. Since lactate is transported from cells together with a proton, acidification of the culture medium (ECAR) is an estimate of lactate production and the glycolytic rate of cells. In the experiment shown in FIG. 6A, ECAR measurements were initiated in the absence of glucose. At point A, glucose was added and ECAR measurements continued. The increase in ECAR upon glucose addition indicates that the change is due to increased glycolysis. At point B, additional glucose along with vehicle (control), DCA plus oxamate, or AT-N4-002 was added. In control cultures the ECAR continued to increase but this increase was completely blocked by either DCA plus oxamate or AT-N4-002. This is shown by a bar graph in FIG. 6B. These results indicate that, in vitro, the prodrugs have similar effects on cancer cell metabolism as equivalent concentrations of DCA and oxamate.

Example 8

Compound AT-N4-002 Sensitizes Tumors to Chemoradiation Treatment and Inhibits Tumor Growth in an HPV+Mouse Model of HNSCC Applicants have shown that DCA combined with oxamate slows tumor growth and enhances survival in immune-competent wild-type mice treated with chemoradiation (FIG. 7A, 7B). To study the effects of the new prodrugs on tumor growth in vivo, C57Bl/6 immune-competent mice were used. Tumors were established on the right flank of the leg. After 11 days, treatment was initiated with daily i.p. injection of vehicle, AT-N4-001, or AT-N4-002. All mice received three rounds of treatment with chemoradiation (CRT: 0.132 mg/mouse cisplatin and 8 Gy radiation, weekly starting at day 11). Tumor volumes were measured weekly. FIG. 8A compares two conditions: 1) DCA oxamate is the control in which mice were treated with CRT+DCA (6 mg/mouse+Oxamate (2.2 mg/mouse. 2) CRT+AT-N4-002 (7.6 mg/mouse) or CRT+AT-N4-001 (7.6 mg/mouse). Importantly, in this experiment DCA and oxamate were given at equal molar ratios that are expected to be delivered by the prodrugs. CRT+AT-N4-001 initially reduced tumor growth compared to CRT+DCA+oxamate control, but this was not maintained over longer times. CRT+AT-N4-002 reduced average tumor growth compared to the control during the entire experiment. FIG. 8B shows that the CRT+AT-N4-002 condition had approximately a 25% improved long-term survival compared to treatment with CRT+DCA+Oxamate These results suggest that the prodrugs have additional properties that are not shared by the simple combination of DCA and oxamate.

Figure 7:
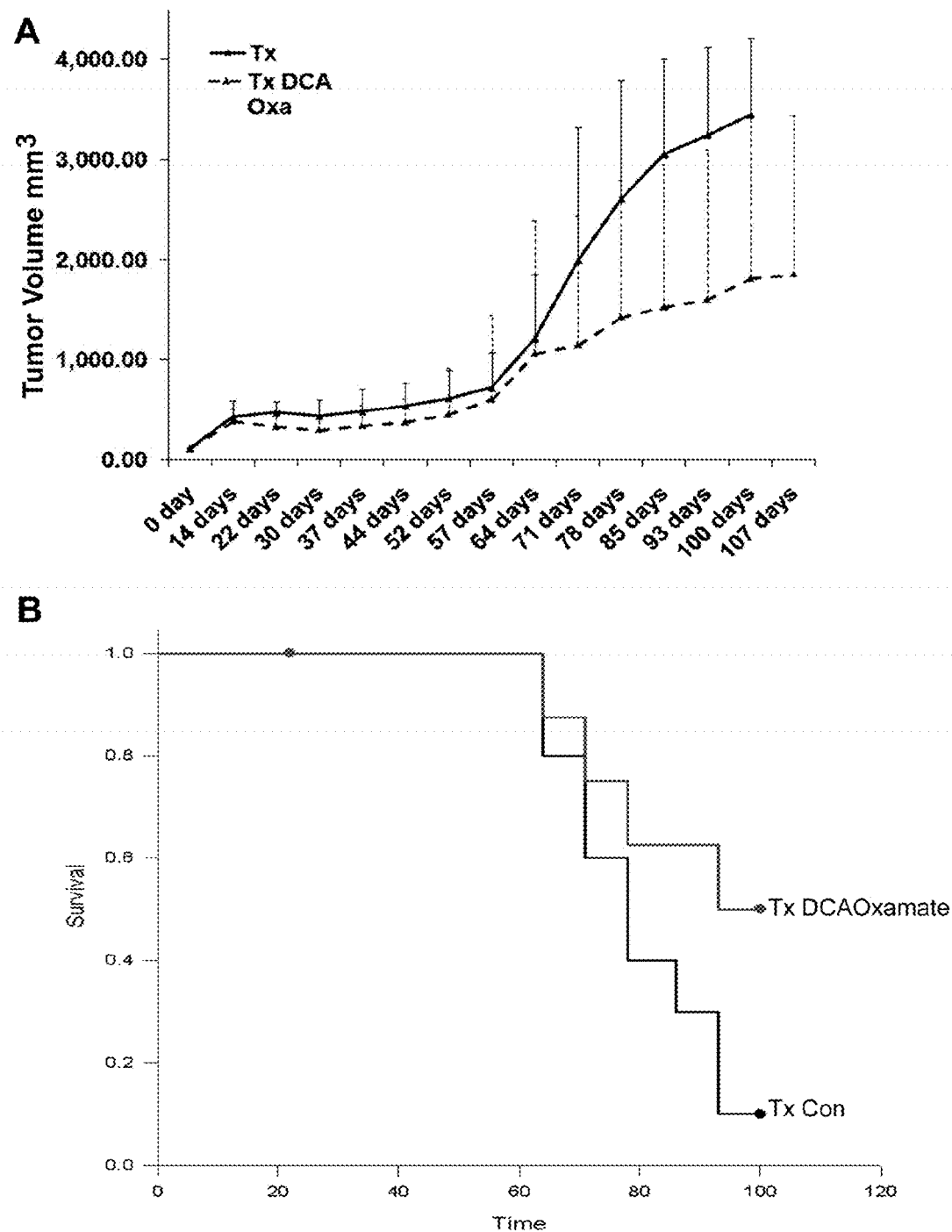
FIG. 7 illustrates the effects of DCA plus oxamate on tumor growth (A) or on survival (B) with HPV+ model of HNSCC in wild-type C57Bl/6 mice. All mice received 3 rounds of cisplatin (0.132 mg/mouse) plus radiation (8 Gy/mouse) treatment (Tx) at weekly intervals starting 14 days after tumor initiation. Mice receiving DCA (6 mg/mouse) plus oxamate (15 mg/mouse) were treated every weekday, starting with the first chemoradiation treatment by i.p. injection.

As background, FIG. 7 shows that, compared to chemoradiation alone, using DCA plus oxamate during chemoradiation slows tumor growth and improves survival in wild-type immune-competent mice. Previous experiments with DCA indicate that it enhances tumor clearance only in immune-competent mice and only in combination with chemoradiation. This suggests that DCA enhances the antitumor immune response that is initiated by cisplatin and radiation treatment.

Figure 9:
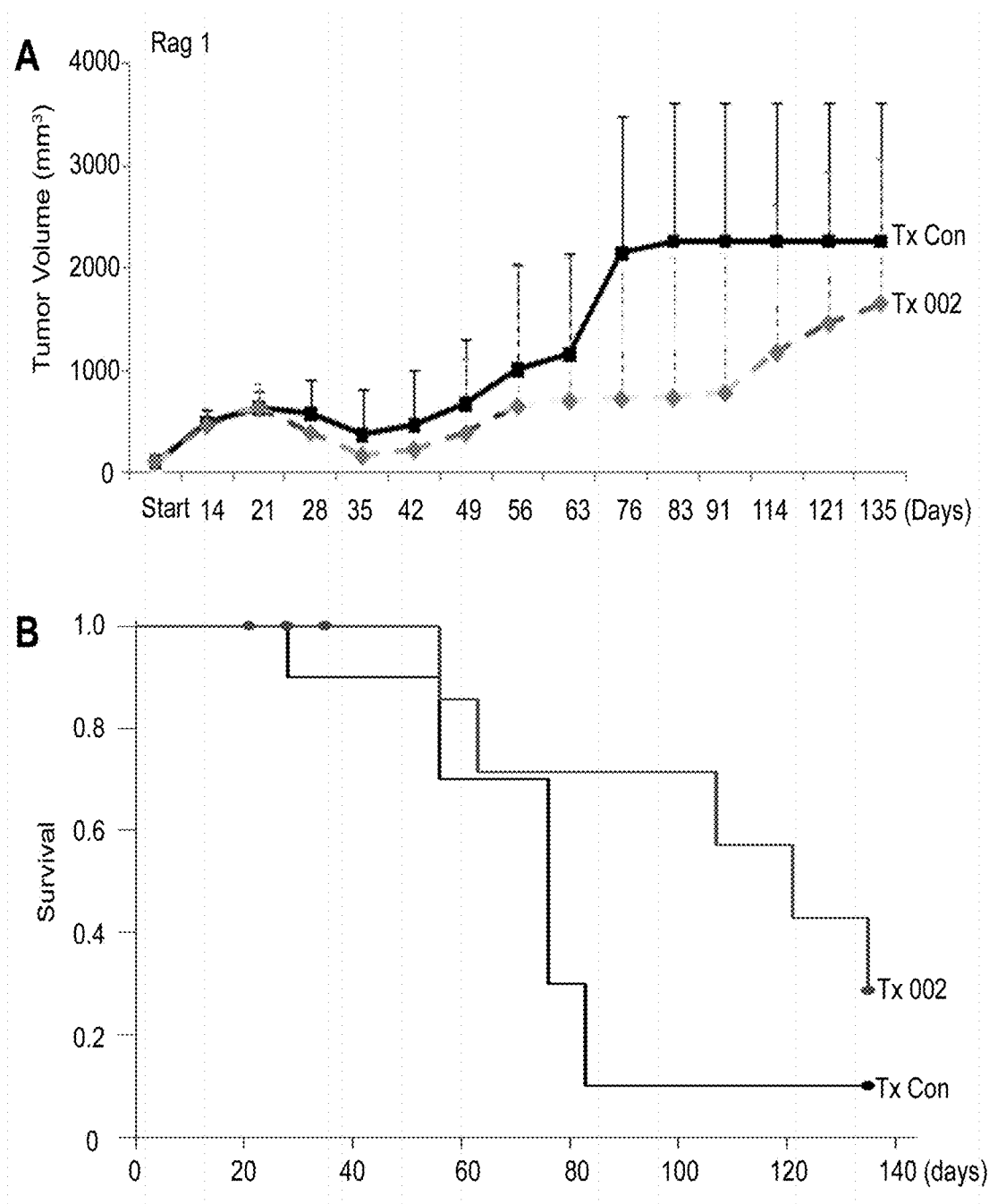
FIG. 9 illustrates the effect of AT-N4-002 prodrug on tumor growth (A) and animal survival (B) in RAG-1 immune-deficient mice. Treatment conditions are the same as those described in FIG. 7.

To examine whether the prodrug AT-N4-002 also requires an immune response to control tumor growth, experiments were performed in RAG-1 mice. Based on our previous experience with DCA, we hypothesized that survival and tumor clearance would not be observed in these immune deficient mice following treatment with AT-N4-002. However, in combination with chemoradiation, AT-N4-002 treatment slowed tumor growth and lengthened survival in RAG-1 mice (FIG. 9). These effects were not as great as those observed in wild-type mice, suggesting that the prodrug has both immune-dependent and immune-independent effects on tumors. These immune-independent effects of AT-N4-002 on tumor growth in immune-deficient mice could be due to direct effects on tumor cell growth or cell death as described in Example 9, below.

Example 9

Figure 10:
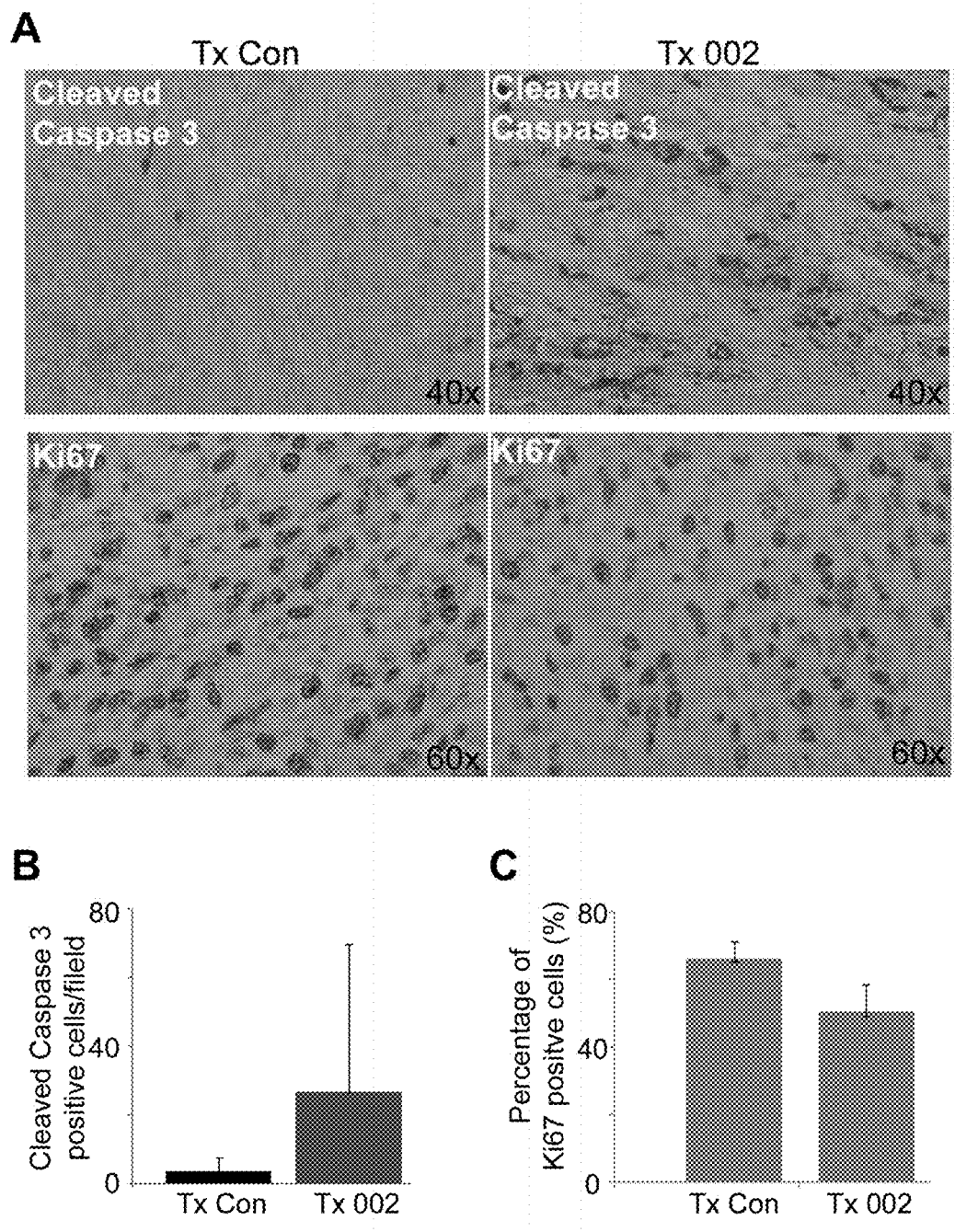
FIG. 10 illustrates Effect of AT-N4-002 on tumor cell apoptosis and cell proliferation. (A) Sections of tumors from mice treated either with chemo-radiation (Tx) or chemoradiation plus AT-N4-002 were subjected to IHC to detect cleaved caspase 3 or Ki67. (B) Cleaved caspase 3 positive cells were counted in 5 random fields from the IHC experiment shown in A. (C) The percent of Ki67 positive cells from the IHC experiment shown in A.

Compound AT-N4-002 Inhibits Proliferation and Enhances Apoptotic Cell Death in Tumors To examine potential direct, immune-independent effects of the prodrug on tumors, tumor bearing wild-type mice were treated for one week with AT-N4-002 plus one round of chemoradiation. Tumors were then harvested and processed for immunohistochemical detection of Ki67, a proliferation marker, and cleaved caspase 3, a marker for apoptosis (FIG. 10). AT-N4-002 plus CRT showed significantly increased cleaved caspase 3 positive cells as compared to CRT alone. In addition, AT-N4-002 treatment appeared to decrease Ki67 positive cells in the tumor. These results indicate that the prodrug promotes cell death and inhibits proliferation of the tumor cells. Such direct effects on the tumor cells could be responsible for the reduced tumor growth observed in immune deficient mice.

Example 10

Figure 11:
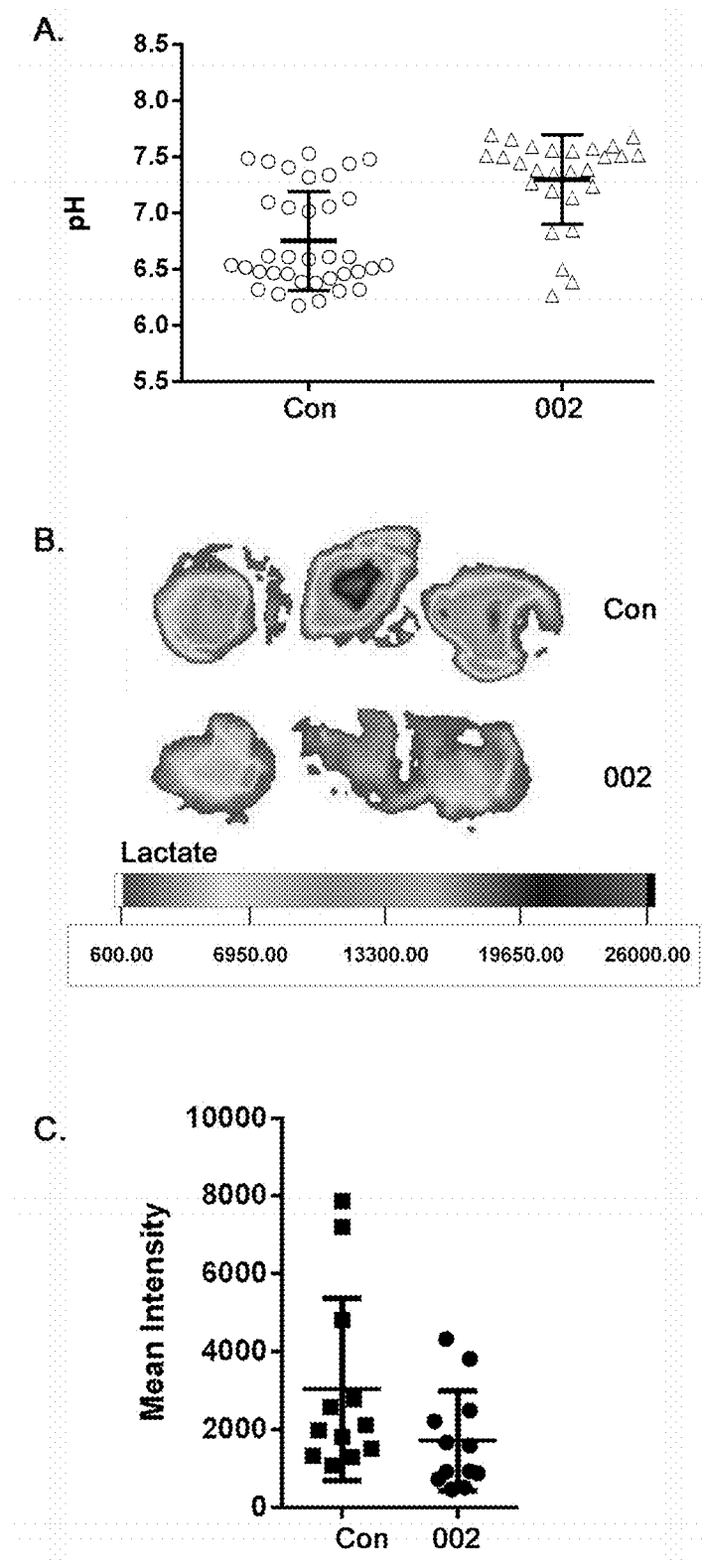
FIG. 11 illustrates the effect of prodrug on tumor pH and tumor lactate. (A) Intratumoral pH in living animals was determined by inserting a needle pH electrode directly into the tumor. The pH was read at 3 different depths in each tumor. Each marker on the graph represents a separate pH measurement. The bar represents the mean and the error bars the standard deviation. (B) Frozen sections of excised tumors were used to estimate lactate levels in the tumor microenvironment. This was performed using the In Vivo Xtreme imager to visualize lactate-dependent luciferase activity as described by Broggini-Tenzer et al. [Metabolism of tumors under treatment: mapping of metabolites with quantitative bioluminescence. Radiother Oncol 99, 398-403 (2011)]. (C) Plot of lactate measurements in B. Each marker represents one tumor. The bar represents the mean and the error bars the standard deviation.

Compound AT-N4-002 Reduces Tumor Lactate Production and Acidification of the Tumor Microenvironment The ability of DCA and oxamate to enhance survival in wild-type mice following chemoradiation correlates closely with their ability to reduce tumor lactate. We therefore examined the ability of the prodrug AT-N4-002 to reduce tumor lactate. Wild-type tumor bearing mice were treated with either CRT or CRT followed by one week of daily ip injection of AT-N4-002. Lactate is exported from cells together with a proton and therefore promotes acidification of the tumor microenvironment. Intratumoral pH was measured with a needle pH electrode. The AT-N4-002 plus CRT group had significantly higher intratumoral pH than the CRT group (FIG. 11A). This correlated with decreased tumor lactate in the AT-N4-002 treated group. (FIG. 11B,C). These results confirm that compound AT-N4-002 inhibits the expected metabolic targets in the tumor cells, leading to reduced lactate production and preventing acidification of the tumor microenvironment.

Example 11

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1 N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraban | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

REFERENCES

1. Jang, M., Kim, S. S., and Lee, J. (2013) Cancer cell metabolism: implications for therapeutic targets. *Experimental & molecular medicine* 45, e45
2. Vander Heiden, M. G., Cantley, L. C., and Thompson, C. B. (2009) Understanding the Warburg effect: the metabolic requirements of cell proliferation. *Science* 324, 1029-1033
3. Gatenby, R. A., and Gillies, R. J. (2004) Why do cancers have high aerobic glycolysis? *Nature reviews. Cancer* 4, 891-899
4. Warburg, O. (1956) On the origin of cancer cells. *Science* 123, 309-314
5. Bailey, K. M., Wojtkowiak, J. W., Hashim, A. I., and Gillies, R. J. (2012) Targeting the metabolic microenvironment of tumors. *Advances in pharmacology* 65, 63-107
6. Kumar, A., Kant, S., and Singh, S. M. (2013) Antitumor and chemosensitizing action of dichloroacetate implicates modulation of tumor microenvironment: a role of reorganized glucose metabolism, cell survival regulation and macrophage differentiation. *Toxicology and applied pharmacology* 273, 196-208
7. Gottfried, E., Kunz-Schughart, L. A., Ebner, S., Mueller-Klieser, W., Hoves, S., Andreesen, R., Mackensen, A., and Kreutz, M. (2006) Tumor-derived lactic acid modulates dendritic cell activation and antigen expression. *Blood* 107, 2013-2021
8. Shime, H., Yabu, M., Akazawa, T., Kodama, K., Matsumoto, M., Seya, T., and Inoue, N. (2008) Tumor-secreted lactic acid promotes IL-23/IL-17 proinflammatory pathway. *Journal of immunology* 180, 7175-7183
9. Goetze, K., Walenta, S., Ksiazkiewicz, M., Kunz-Schughart, L. A., and Mueller-Klieser, W. (2011) Lactate enhances motility of tumor cells and inhibits monocyte migration and cytokine release. *International journal of oncology* 39, 453-463
10. Remillard, C. V., and Yuan, J. X. (2004) Activation of K+ channels: an essential pathway in programmed cell death. *American journal of physiology. Lung cellular and molecular physiology* 286, L49-67
11. Bonnet, S., Archer, S. L., Allalunis-Turner, J., Haromy, A., Beaulieu, C., Thompson, R., Lee, C. T., Lopaschuk, G. D., Puttagunta, L., Bonnet, S., Harry, G., Hashimoto, K., Porter, C. J., Andrade, M. A., Thebaud, B., and Michelakis, E. D. (2007) A mitochondria-K+ channel axis is suppressed in cancer and its normalization promotes apoptosis and inhibits cancer growth. *Cancer cell* 11, 37-51
12. Ruckenstuhl, C., Buttner, S., Carmona-Gutierrez, D., Eisenberg, T., Kroemer, G., Sigrist, S. J., Frohlich, K. U., and Madeo, F. (2009) The Warburg effect suppresses oxidative stress induced apoptosis in a yeast model for cancer. *PloS one* 4, e4592
13. Buzzai, M., Bauer, D. E., Jones, R. G., Deberardinis, R. J., Hatzivassiliou, G., Elstrom, R. L., and Thompson, C. B. (2005) The glucose dependence of Akt-transformed cells can be reversed by pharmacologic activation of fatty acid beta-oxidation. *Oncogene* 24, 4165-4173
14. Elstrom, R. L., Bauer, D. E., Buzzai, M., Karnauskas, R., Harris, M. H., Plas, D. R., Zhuang, H., Cinalli, R. M., Alavi, A., Rudin, C. M., and Thompson, C. B. (2004) Akt stimulates aerobic glycolysis in cancer cells. *Cancer research* 64, 3892-3899
15. Bensaad, K., Tsuruta, A., Selak, M. A., Vidal, M. N., Nakano, K., Bartrons, R., Gottlieb, E., and Vousden, K. H. (2006) TIGAR, a p53-inducible regulator of glycolysis and apoptosis. *Cell* 126, 107-120
16. Hu, Y., Lu, W., Chen, G., Wang, P., Chen, Z., Zhou, Y., Ogasawara, M., Trachootham, D., Feng, L., Pelicano, H., Chiao, P. J., Keating, M. J., Garcia-Manero, G., and Huang, P. (2012) K-ras (G12V) transformation leads to mitochondrial dysfunction and a metabolic switch from oxidative phosphorylation to glycolysis. *Cell research* 22, 399-412
17. Loscalzo, J. (2010) The cellular response to hypoxia: tuning the system with microRNAs. *The Journal of clinical investigation* 120, 3815-3817
18. Semenza, G. L. (2011) Hypoxia-inducible factor 1: regulator of mitochondrial metabolism and mediator of ischemic preconditioning. *Biochimica et biophysica acta* 1813, 1263-1268
19. Ke, Q., and Costa, M. (2006) Hypoxia-inducible factor-1 (HIF-1). *Molecular pharmacology* 70, 1469-1480
20. Brahimi-Horn, M. C., Ben-Hail, D., Hie, M., Gounon, P., Rouleau, M., Hofman, V., Doyen, J., Mari, B., Shoshan-Barmatz, V., Hofman, P., Pouyssegur, J., and Mazure, N. M. (2012) Expression of a truncated active form of VDAC1 in lung cancer associates with hypoxic cell survival and correlates with progression to chemotherapy resistance. *Cancer research* 72, 2140-2150
21. Aykin-Burns, N., Slane, B. G., Liu, A. T., Owens, K. M., O'Malley, M. S., Smith, B. J., Domann, F. E., and Spitz, D. R. (2011) Sensitivity to low-dose/low-LET ionizing radiation in mammalian cells harboring mutations in succinate dehydrogenase subunit C is governed by mitochondria-derived reactive oxygen species. *Radiation research* 175, 150-158
22. Kluza, J., Corazao-Rozas, P., Touil, Y., Jendoubi, M., Maire, C., Guerreschi, P., Jonneaux, A., Ballot, C., Balayssac, S., Valable, S., Corroyer-Dulmont, A., Bernaudin, M., Malet-Martino, M., de Lassalle, E. M., Maboudou, P., Formstecher, P., Polakowska, R., Mortier, L., and Marchetti, P. (2012) Inactivation of the HIF-1alpha/PDK3 signaling axis drives melanoma toward mitochondrial oxidative metabolism and potentiates the therapeutic activity of pro-oxidants. *Cancer research* 72, 5035-5047
23. Garon, E. B., Christofk, H. R., Hosmer, W., Britten, C. D., Bahng, A., Crabtree, M. J., Hong, C. S., Kamranpour, N., Pitts, S., Kabbinavar, F., Patel, C., von Euw, E., Black, A., Michelakis, E. D., Dubinett, S. M., and Slamon, D. J. (2014) Dichloroacetate should be considered with platinum-based chemotherapy in hypoxic tumors rather than as a single agent in advanced non-small cell lung cancer. *Journal of cancer research and clinical oncology* 140, 443-452
24. Abdelmalak, M., Lew, A., Ramezani, R., Shroads, A. L., Coats, B. S., Langaee, T., Shankar, M. N., Neiberger, R. E., Subramony, S. H., and Stacpoole, P. W. (2013) Long-term safety of dichloroacetate in congenital lactic acidosis. *Molecular genetics and metabolism* 109, 139-143
25. Michelakis, E. D., Sutendra, G., Dromparis, P., Webster, L., Haromy, A., Niven, E., Maguire, C., Gammer, T. L., Mackey, J. R., Fulton, D., Abdulkarim, B., McMurtry, M. S., and Petruk, K. C. (2010) Metabolic modulation of glioblastoma with dichloroacetate. *Science translational medicine* 2, 31ra34
26. Michelakis, E. D., Webster, L., and Mackey, J. R. (2008) Dichloroacetate (DCA) as a potential metabolic-targeting therapy for cancer. *British journal of cancer* 99, 989-994
27. Morfouace, M., Lalier, L., Bahut, M., Bonnamain, V., Naveilhan, P., Guette, C., Oliver, L., Gueguen, N., Reynier, P., and Vallette, F. M. (2012) Comparison of spheroids formed by rat glioma stem cells and neural stem cells reveals differences in glucose metabolism and promising therapeutic applications. *The Journal of biological chemistry* 287, 33664-33674
28. Saed, G. M., Fletcher, N. M., Jiang, Z. L., Abu-Soud, H. M., and Diamond, M. P. (2011) Dichloroacetate induces apoptosis of epithelial ovarian cancer cells through a mechanism involving modulation of oxidative stress. *Reproductive sciences* 18, 1253-1261
29. Ayyanathan, K., Kesaraju, S., Dawson-Scully, K., and Weissbach, H. (2012) Combination of sulindac and dichloroacetate kills cancer cells via oxidative damage. *PloS one* 7, e39949
30. Fiebiger, W., Olszewski, U., Ulsperger, E., Geissler, K., and Hamilton, G. (2011) In vitro cytotoxicity of novel platinum-based drugs and dichloroacetate against lung carcinoid cell lines. *Clinical & translational oncology: official publication of the Federation of Spanish Oncology Societies and of the National Cancer Institute of Mexico* 13, 43-49
31. Xuan, Y., Hur, H., Ham, I. H., Yun, J., Lee, J. Y., Shim, W., Kim, Y. B., Lee, G., Han, S. U., and Cho, Y. K. (2014) Dichloroacetate attenuates hypoxia-induced resistance to 5-fluorouracil in gastric cancer through the regulation of glucose metabolism. *Experimental cell research* 321, 219-230
32. Dunbar, E. M., Coats, B. S., Shroads, A. L., Langaee, T., Lew, A., Forder, J. R., Shuster, J. J., Wagner, D. A., and Stacpoole, P. W. (2013) Phase 1 trial of dichloroacetate (DCA) in adults with recurrent malignant brain tumors. *Investigational new drugs*
33. Papaconstantinou, J., and Colowick, S. P. (1961) The role of glycolysis in the growth of tumor cells. II. The effect of oxamic acid on the growth of HeLa cells in tissue culture. *The Journal of biological chemistry* 236, 285-288
34. Papaconstantinou, J., and Colowick, S. P. (1961) The role of glycolysis in the growth of tumor cells. I. Effects of oxamic acid on the metabolism of Ehrlich ascites tumor cells in vitro. *The Journal of biological chemistry* 236, 278-284
35. Granchi, C., Bertini, S., Macchia, M., and Minutolo, F. (2010) Inhibitors of lactate dehydrogenase isoforms and their therapeutic potentials. *Current medicinal chemistry* 17, 672-697
36. Le, A., Cooper, C. R., Gouw, A. M., Dinavahi, R., Maitra, A., Deck, L. M., Royer, R. E., Vander Jagt, D. L., Semenza, G. L., and Dang, C. V. (2010) Inhibition of lactate dehydrogenase A induces oxidative stress and inhibits tumor progression. *Proceedings of the National Academy of Sciences of the United States of America* 107, 2037-2042
37. Semenza, G. L. (2008) Tumor metabolism: cancer cells give and take lactate. *The Journal of clinical investigation* 118, 3835-3837
38. Sonveaux, P., Vegran, F., Schroeder, T., Wergin, M. C., Verrax, J., Rabbani, Z. N., De Saedeleer, C. J., Kennedy, K. M., Diepart, C., Jordan, B. F., Kelley, M. J., Gallez, B., Wahl, M. L., Feron, O., and Dewhirst, M. W. (2008) Targeting lactate-fueled respiration selectively kills hypoxic tumor cells in mice. *The Journal of clinical investigation* 118, 3930-3942
39. Goldberg, E. B., and Colowick, S. P. (1965) The Role of Glycolysis in the Growth of Tumor Cells. 3. Lactic Dehydrogenase as the Site of Action of Oxamate on the Growth of Cultured Cells. *The Journal of biological chemistry* 240, 2786-2790
40. Goldberg, E. B., Nitowsky, H. M., and Colowick, S. P. (1965) The Role of Glycolysis in the Growth of Tumor Cells. Iv. The Basis of Glucose Toxicity in Oxamate-Treated, Cultured Cells. *The Journal of biological chemistry* 240, 2791-2796
41. Zhai, X., Yang, Y., Wan, J., Zhu, R., and Wu, Y. (2013) Inhibition of LDH-A by oxamate induces G2/M arrest, apoptosis and increases radiosensitivity in nasopharyngeal carcinoma cells. *Oncology reports* 30, 2983-2991
42. Fiume, L., Manerba, M., Vettraino, M., and Di Stefano, G. (2010) Impairment of aerobic glycolysis by inhibitors of lactic dehydrogenase hinders the growth of human hepatocellular carcinoma cell lines. *Pharmacology* 86, 157-162
43. Fiume, L., Vettraino, M., Manerba, M., and Di Stefano, G. (2011) Inhibition of lactic dehydrogenase as a way to increase the anti-proliferative effect of multi-targeted kinase inhibitors. *Pharmacological research: the official journal of the Italian Pharmacological Society* 63, 328-334
44. Li, X., Lu, W., Hu, Y., Wen, S., Qian, C., Wu, W., and Huang, P. (2013) Effective inhibition of nasopharyngeal carcinoma in vitro and in vivo by targeting glycolysis with oxamate. *International journal of oncology* 43, 1710-1718

45. Zhou, M., Zhao, Y., Ding, Y., Liu, H., Liu, Z., Fodstad, O., Riker, A. I., Kamarajugadda, S., Lu, J., Owen, L. B., Ledoux, S. P., and Tan, M. (2010) Warburg effect in chemosensitivity: targeting lactate dehydrogenase-A resensitizes taxol-resistant cancer cells to taxol. *Molecular cancer* 9, 33

46. Coppock, J. D., Wieking, B. G., Molinolo, A. A., Gutkind, J. S., Miskimins, W. K., and Lee, J. H. (2013) Improved clearance during treatment of HPV-positive head and neck cancer through mTOR inhibition. *Neoplasia* 15, 620-630

47. Choi, S. R., Beeler, A. B., Pradhan, A., Watkins, E. B., Rimoldi, J. M., Tekwani, B., and Avery, M. A. (2007) Generation of oxamic acid libraries: Antimalarials and inhibitors of Plasmodium falciparum lactate dehydrogenase. *J Comb Chem* 9, 292-300

48. Paris, G. Y., Garmaise, D. L., Cimon, D. G., Swett, L., Carter, G. W., and Young, P. (1979) Glycerides as prodrugs. 1. Synthesis and antiinflammatory activity of 1,3-bis(alkanoyl)-2-(O-acetylsalicyloyl)glycerides (aspirin triglycerides). *Journal of medicinal chemistry* 22, 683-687

49. Paris, G. Y., Garmaise, D. L., Cimon, D. G., Swett, L., Carter, G. W., and Young, P. (1980) Glycerides as prodrugs. 3. Synthesis and antiinflammatory activity of [1-(p-chlorobenzoyl)-5-methoxy-2-methylindole-3-acetyl]glycerides (indomethacin glycerides). *Journal of medicinal chemistry* 23, 9-13

50. Paris, G. Y., Garmaise, D. L., Cimon, D. G., Swett, L., Carter, G. W., and Young, P. (1980) Glycerides as prodrugs. 2. 1,3-Dialkanoyl-2-(2-methyl-4-oxo-1,3-benzodioxan-2-yl)glycerides (cyclic aspirin triglycerides) as antiinflammatory agents. *Journal of medicinal chemistry* 23, 79-82

51. Koukourakis, M. I., Giatromanolaki, A., Winter, S., Leek, R., Sividris, E., and Harris, A. L. (2009) Lactate dehydrogenase 5 expression in squamous cell head and neck cancer relates to prognosis following radical or postoperative radiotherapy. *Oncology* 77, 285-292

52. Kailavasan, M., Rehman, I., Reynolds, S., Bucur, A., Tozer, G., and Paley, M. (2014) NMR-based evaluation of the metabolic profile and response to dichloroacetate of human prostate cancer cells. *NMR in biomedicine*

53. Duan, Y., Zhao, X., Ren, W., Wang, X., Yu, K. F., Li, D., Zhang, X., and Zhang, Q. (2013) Antitumor activity of dichloroacetate on C6 glioma cell: in vitro and in vivo evaluation. *OncoTargets and therapy* 6, 189-198

54. Pathak, R. K., Marrache, S., Harn, D. A., and Dhar, S. (2014) Mito-DCA: A Mitochondria Targeted Molecular Scaffold for Efficacious Delivery of Metabolic Modulator Dichloroacetate. *ACS chemical biology*

55. Liu, D., Wang, F., Yue, J., Jing, X., and Huang, Y. (2013) Metabolism targeting therapy of dichloroacetate-loaded electrospun mats on colorectal cancer. *Drug delivery*

56. Hoover, A. C., Spanos, W. C., Harris, G. F., Anderson, M. E., Klingelhutz, A. J., and Lee, J. H. (2007) The role of human papillomavirus 16 E6 in anchorage-independent and invasive growth of mouse tonsil epithelium. *Arch Otolaryngol* 133, 495-502

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound:

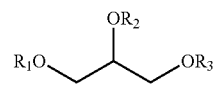

wherein $R_1$ and $R_2$ are each dichloroacetate, and $R_3$ is H, oxamate, —C(O)C(O)N($R_4$)($R_5$), dichloroacetate, or R*, wherein R* is a diacid, an amino acid, an alkyl group, an aryl group, a heterocyclic group, or a pharmaceutically acceptable salt thereof, wherein $R_4$ and $R_5$ are each independently a ($C_1$-$C_{20}$)alkyl group, a ($C_3$-$C_{16}$)cycloalkyl group, a ($C_6$-$C_{14}$)aryl group, furan, pyridine, imidazole, or a pharmaceutically acceptable salt thereof.

2. A compound:

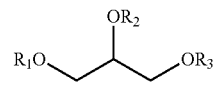

wherein $R_1$ and $R_3$ are each dichloroacetate, and $R_2$ is H, oxamate, dichloroacetate, —C(O)CCl3, C(O)$CH_2$Cl, or R*, wherein R* is a diacid, an amino acid, an alkyl group, an aryl group, a heterocyclic group, or a pharmaceutically acceptable salt thereof.

3. A compound:

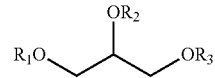

wherein $R_1$ is dichloroacetate, and $R_2$ and $R_3$ are each oxamate or —C(O)C(O)N($R_4$)($R_5$), wherein $R_4$ and $R_5$ are each independently a ($C_1$-$C_{20}$)alkyl group, a ($C_3$-$C_{16}$)cycloalkyl group, a ($C_6$-$C_{14}$)aryl group, furan, pyridine, imidazole, or a pharmaceutically acceptable salt thereof.

4. A pharmaceutical composition comprising one or more compounds of claim 1, 2 or 3, or the pharmaceutically acceptable salts thereof; and a pharmaceutically acceptable carrier.

5. A pharmaceutical composition comprising an amount of at least one compound of claim 1, 2 or 3, and an amount of dichloroacetate, or a pharmaceutically acceptable salt thereof; and a pharmaceutically acceptable carrier.

* * * * *